(12) United States Patent
Lench et al.

(10) Patent No.: US 11,869,630 B2
(45) Date of Patent: Jan. 9, 2024

(54) SCREENING SYSTEM AND METHOD FOR DETERMINING A PRESENCE AND AN ASSESSMENT SCORE OF CELL-FREE DNA FRAGMENTS

(71) Applicant: CONGENICA LTD., Cambridge (GB)

(72) Inventors: Nicholas Lench, Cambridge (GB); Matt Hurles, Cambridge (GB); John McGonigle, Cambridge (GB); Alan Martin, Cambridge (GB); Suzanne Drury, Cambridge (GB)

(73) Assignee: CONGENICA LTD., Cambridge (GB)

( * ) Notice: Subject to any disclaimer, the term of this patent is extended or adjusted under 35 U.S.C. 154(b) by 1029 days.

(21) Appl. No.: 16/632,071

(22) PCT Filed: Jul. 18, 2018

(86) PCT No.: PCT/EP2018/069559
§ 371 (c)(1),
(2) Date: Jan. 17, 2020

(87) PCT Pub. No.: WO2019/016289
PCT Pub. Date: Jan. 24, 2019

(65) Prior Publication Data
US 2021/0027856 A1    Jan. 28, 2021

(30) Foreign Application Priority Data

Jul. 18, 2017  (GB) ..................... 1711523
Jul. 18, 2017  (GB) ..................... 1711528
Jul. 18, 2017  (GB) ..................... 1711536
Jul. 18, 2017  (GB) ..................... 1711540

(51) Int. Cl.
G16B 20/20    (2019.01)
G16B 20/50    (2019.01)
G16B 30/00    (2019.01)

(52) U.S. Cl.
CPC ............. *G16B 20/20* (2019.02); *G16B 20/50* (2019.02); *G16B 30/00* (2019.02)

(58) Field of Classification Search
CPC ........ G16B 20/20; G16B 20/50; G16B 30/00; G16B 20/00
See application file for complete search history.

(56) References Cited

U.S. PATENT DOCUMENTS

| | | |
|---|---|---|
| 2011/0288780 A1 | 11/2011 | Rabinowitz et al. |
| 2016/0115471 A1 | 4/2016 | Kim et al. |

FOREIGN PATENT DOCUMENTS

| | | | | |
|---|---|---|---|---|
| CA | 2877331 A1 | * | 12/2013 | ........... C12Q 1/6809 |
| JP | 2004126857 A | | 4/2004 | |
| WO | 9517524 A2 | | 6/1995 | |
| WO | 2007113490 A1 | | 10/2007 | |
| WO | 2013109981 A1 | | 7/2013 | |
| WO | 2014099919 A2 | | 6/2014 | |
| WO | 2015026967 A1 | | 2/2015 | |
| WO | 2016057901 A1 | | 4/2016 | |

OTHER PUBLICATIONS

Wright D. Ultrasound in Obstetric and Gynecology 45: 48-54. (Year: 2015).*
Kagan KO. Ultrasound in Obstetric and Gynecology 51: 437-444. (Year: 2018).*
Snyder MW. Prenatal Diagnosis 33: 547-554. (Year: 2013).*
Xia L. bioRxiv 089813. (Year: 2016).*
Xu Y. Genetics in Medicine 17(11): 889-896 (Year: 2015).*
NIMH. Gene readouts contribute to distinctness of mental disorders. Press release. 2019. https://www.nimh.nih.gov/news/science-news/2021/gene-readouts-contribute-to-distinctness-of-mental-disorders(Year: 2021).*
Chan et al. "Second generation noninvasive fetal genome analysis reveals de novo mutations, single-base parental inheritance, and preferred DNA ends" PNAS vol. 113, Dec. 13, 2016, Epub Oct. 31, 2016 Retrieved from https://www.ncbi.nlm.nih.gov/pubmed/27799561, DOI: 10.1073/pnas. 1615800113, 2 pages.
Chan et al. "Size Distributions of Maternal and Fetal DNA in Maternal Plasma." Clinical Chemistry, vol. 50 issue 1, 2004, 5 pages.
GB Intellectual Property Office, Combined Search and Examination Report under Sections 17 and 18(3), Application No. GB1711523.9, dated Apr. 30, 2018, pp. 88-92, 6 pages.
GB Intellectual Property Office, Combined Search and Examination Report under Sections 17 and 18(3), Application No. GB1711536.1, dated May 1, 2018, 9 pages.
GB Intellectual Property Office, Search Report Under Section 17, Application No. GB1711528.8, dated Jan. 16, 2018, 4 pages.
International Search Report, Application No. PCT/EP2018/069559, dated Jan. 8, 2019, 6 pages.

(Continued)

*Primary Examiner* — G. Steven Vanni
*Assistant Examiner* — Robert James Kallal
(74) *Attorney, Agent, or Firm* — Ziegler IP Law Group, LLC

(57) ABSTRACT

A prenatal screening system includes a wet-laboratory arrangement and a data processing arrangement to exchange instructions and data with the wet-laboratory arrangement. The data processing arrangement includes a database arrangement storing genetic information accessible to one or more algorithms executable on the data processing arrangement. The wet-laboratory arrangement collects one or more maternal blood samples from a pregnant mother. The wet-laboratory arrangement isolates free fetal DNA fragments present in cell-free DNA derived from plasma of the one or more maternal blood samples. The isolation utilizes baits based upon coordinates of cell-free fetal DNA fragment specific end-points, and the data processing arrangement analyses the isolated free fetal DNA and compares with one or more DNA templates stored in the data processing arrangement for determining an occurrence of one or more biological characteristics of fetal DNA present in the one or more maternal blood samples.

18 Claims, 12 Drawing Sheets

(56) References Cited

OTHER PUBLICATIONS

Thessalia Papasavva et al. "Next generation sequencing of SNPs for non-invasive prenatal diagnosis: challenges and feasibility as illustrated by an application to [beta]-thalassaemia", European Journal of Human Genetics., vol. 21, No. 12 Apr. 10, 2013, ISSN: 1018-4813, DOI: 10.1038/ejhg.2013.47 pp. 1403-1410.

Yang et al, "Size-selective separation and overall-amplification of cell-free fetal DNA fragments using PCR-based enrichment." Scientific Reports, Published Online Jan. 19, 2017, doi: 10.1038/srep40936, 17 pages.

\* cited by examiner

SCREENING SYSTEM AND METHOD FOR DETERMINING A PRESENCE AND AN ASSESSMENT SCORE OF CELL-FREE DNA FRAGMENTS

TECHNICAL FIELD

The present disclosure relates to screening systems and methods; in particular, the present disclosure relates to non-invasive prenatal screening systems and methods of (for) prenatal screening, for example to prenatal screening systems and methods that process maternal blood in order to determine fetal (foetal) characteristics and to prenatal screening systems and methods that utilize a targeted assay approach (for example utilizing a knowledgebase), for example to prenatal screening systems that process maternal blood in order to determine fetal (foetal) characteristics. Moreover, the present disclosure concerns methods of (for) using aforementioned screening systems, for example to methods of (for) using aforementioned screening systems to process maternal blood in order to determine fetal (foetal) characteristics. Additionally, the present disclosure is concerned with computer program products comprising a non-transitory computer-readable storage medium having computer-readable instructions stored thereon, the computer-readable instructions being executable by a computerized device comprising processing hardware to execute the aforesaid methods.

BACKGROUND

Zygote formation and associated subsequent fetal (alternative spelling: foetal) development is a complex biological process that does not always occur without defects arising. It is of great societal benefit that such defects are detected reliably, for example as early as possible, during fetal growth.

Conventionally, antenatal or prenatal screening is provided to pregnant women to determine or treat potential health problems that may occur during pregnancy. Such problems may affect both a given mother and/or the given mother's fetus (alternative spelling: foetus) and may be determined by factors such as lifestyle, environment or genetics, or a combination thereof. However, of particular importance are fetal abnormalities that are genetic in origin. These abnormalities may be caused by mutations inherited from one or both parents (namely, of paternal and/or maternal origin) or may arise spontaneously in a stochastic manner (namely arising "de novo", namely new spontaneous mutations). The nature of such mutations can range extensively, for example from changes in single nucleotides to the presence of additional whole chromosomes (aneuploidy), short tandem repeats and mitochondrial DNA mutations. A nucleotide is an organic molecule consisting of a nitrogenous heterocyclic nucleobase (namely a purine or a pyrimidine), a pentose sugar (deoxyribose in DNA or ribose in RNA), and a phosphate or polyphosphate group, wherein the nucleotides form "rungs" in a DNA double-helix. An example of particular clinical significance are the chromosomal disorders known as aneuploidies that occur when there is an abnormal number of chromosomes (e.g. Down's Syndrome); aneuploidy is a presence of an abnormal number of chromosomes in a cell, for example a human cell having 45 or 47 chromosomes, instead of the usual 46 chromosomes. Many chromosomal disorders are incompatible with life or result in multiple congenital anomalies for a given new born child.

Conventionally known prenatal screening systems and methods for (of) detecting fetal abnormalities use fetal samples derived by invasive techniques such as amniocentesis and chorionic villus sampling. These invasive techniques require careful handling and present a degree of risk to the mother and to the mother's pregnancy.

Prenatal screening for risk of fetal chromosomal abnormalities during pregnancy is available through public and private healthcare providers. This prenatal screening is normally carried out around the first trimester of a given pregnancy (normally between 8 to 14 weeks of the given pregnancy) and typically involves executing a maternal blood test on a given mother. This prenatal screening can consist of the Combined Test or a quadruple blood test. Increasingly an alternative test known as non-invasive prenatal testing is available either as a first line alternative to the combined test, or as a contingency test.

If a pregnancy is categorised as being 'high-risk', an invasive diagnostic procedure (e.g. chorionic villus sampling, amniocentesis, cordocentesis) is offered to the mother to confirm or rule out:

(a) Down's syndrome (trisomy chromosome 21-T21);
(b) Edwards's syndrome (trisomy chromosome 18-T18); and
(c) Patau syndrome (trisomy chromosome 13-T13).

Invasive tests such as chorionic villus sampling and amniocentesis involve sampling from chorionic villus (placental tissue) and amniotic sac containing fetal tissues for prenatal diagnosis of chromosomal abnormalities. Placental tissue can be subject to confined placental mosaicism, meaning results from such sampling from chorionic villus can be very difficult to assess accurately.

Pregnant women are also offered a second ultrasound scan at 18 to 21 weeks into gestation to check for structural fetal anomalies such as cardiac malformations, brain malformations and skeletal abnormalities. This second scan can be used to direct antenatal treatments, for identifying anomalies that require early intervention following delivery or enable follow-on diagnostic testing and pregnancy management. Invasive tests such as chorionic villus sampling, amniocentesis and cordocentesis carry a 1% chance of miscarriage and are therefore only executed when there is an enhanced risk of abnormalities occurring.

During recent years, non-invasive techniques (without an associated risk of miscarriage) have been developed for the diagnoses of fetal chromosomal anomalies that rely on the presence of circulating cell free fetal DNA in the mother's blood. Such testing of cell-free fetal DNA (cffDNA) has now entered routine clinical practice for non-invasive prenatal testing (NIPT) for aneuploidy (T21, T18, T13). The number of anomalies that can be tested by NIPT are increasing as methods are developed for the identification of sub-chromosomal rearrangements such as 22q11.2/DiGeorge syndrome and other microdeletion syndromes. However, the false positive rate (namely false positive assessment risk of there being a defect) for these anomalies is considered to be too high to offer on a screening basis and it is recommended that it is only offered if there is an accompanying clinical indication such as a congenital heart defect. NIPT is classified as 'testing' rather than 'diagnosis', because the cffDNA which is measured is derived from the placenta rather than the fetus, meaning that false positives can occur due to confined placental mosaicism; 'confined placental mosaicism' (CPM) represents a discrepancy between a chromosomal makeup of cells in a given placenta and cells of a corresponding fetus. For this reason, it is recommended that positive NIPT results are confirmed by an invasive amniocentesis.

Non-invasive prenatal diagnosis (NIPD) is generally classified as a diagnostic assay, wherein a subsequent invasive assay is not required to confirm results from the NIPD. The use of NIPD is more limited than aforementioned non-invasive prenatal testing (NIPT) and is commonly used for fetuses at risk of single gene disorders (namely, inherited and 'de novo' mutations) or who present with a suspicion of a genetic disorder on fetal ultrasound.

Accurately reconstructing genetic information of a given fetus from circulating cffDNA present in a sample of corresponding maternal blood is an exceptionally challenging task, technically. This task is challenging at least in part because cffDNA occurs only as small fragments in the sample and represents only a small fraction of the total cfDNA present in the sample of maternal blood. It is known that cell-free fetal DNA (cffDNA) circulates in maternal blood at a concentration of approximately 10% of a maternal cell-free component. Such cell-free fetal DNA (cffDNA) potentially results from fetal cell apoptosis, placental cell apoptosis and similar cellular metabolic processes. Coupled with low concentrations of total cell free DNA, using next generation sequencing library preparation methods for analysing such cell-free fetal DNA (cffDNA) is challenging due to the need for next generation sequencing library preparation methods to measure small quantities of fetal DNA. Furthermore, using next generation sequencing library preparation methods is challenging for two reasons:

(1) it is difficult to identify genuine 'de novo' variants in fetal DNA (namely, there may arise problems of differentiating variants of DNA); and (2) it is difficult to determine an overrepresentation of fetal alleles which are shared with the mother (wherein, an allele is a variant form of a given gene).

Such difficulties give rise to stochastic noise in measurements that are susceptible to being contributory factors that increase a risk of a false positive or false negative when computing a risk score during prenatal screening.

With respect to the aforementioned challenges, firstly due to errors that are introduced by Polymerase Chain Reaction (PCR) and bridge amplification in sequencing, the 'de novo' variant frequency may be lower or at the same level as the fetal fraction. This error can cause false-positive and false negative results in the aforesaid risk score. Secondly, the lower the fetal fraction, the greater sequencing depth is required to determine whether or not there is over-, under- or equal-representation of a mutation/allele, to establish the zygosity of a fetus at that point. The amount of sequencing performed can be increased, but this has a cost and time implication when seeking to deliver a prenatal screening service.

In known testing systems, the problem of there being only relatively small amounts of fetal DNA in the presence of excess maternal DNA has been addressed by employing several approaches:

(i) by using formaldehyde in blood collection tubes (Dhallan et al., 2004), wherein the use of formaldehydes reduces cell lysis (namely, the breaking down of a membrane of a given cell) and which relatively increases the percentage of free fetal DNA (cffDNA) in samples of maternal blood;

(ii) by using gel size selection to enrich for short fragments of cffDNA, it has been shown to improve the sensitivity of paternal allele detection for β-thalassemia mutations (Li et al., 2005), wherein DNA is size sorted by employing gel electrophoresis and subsequently performing gel excision and associated DNA extraction. However, such an approach is not an amenable procedure for high throughput diagnostics, and hence commercially unsuitable when performing prenatal screening;

(iii) by counting short DNA molecules only, using PCR which preferentially amplifies short and long amplicons (Lun et al., 2008); and (iv) by employing enrichment via use of aforementioned PCR (Yang et al., 2017)

However, enrichment based on size has not yet found a place in contemporary routine clinical practice. Whilst there are distinct populations of maternal and fetal DNA fragment sizes, there is also a considerable region of overlap in fragment sizes, so a complete separation of the two populations is not possible. Such a lack of complete separation effectively increases stochastic noise in measurement that adversely influences a final risk score computed when performing prenatal screen, namely increases a risk of false-positives or false-negatives.

Aforementioned cffDNA is actually derived from a placenta of the mother, not directly from the given fetus (foetus), and thus can display upon sequencing different genetic information to that of the given fetus; such different genetic information can arise from confined placental mosaicism that complicates a process of predicting genetic information of the given fetus, namely a 'child's genome'. Additionally, cffDNA is non-uniformly distributed across a given human genome, and as half of a given child's genome is derived from its mother, a considerable difficulty arises in practice when estimating an extent to which there is identified cffDNA coverage across the given genome. Added to this difficulty, there arise systematic and methodological difficulties that not all regions of the given genome are equally easy to sequence and accurately call, and that errors can be introduced to an underlying determined sequence during associated library preparation and template amplification stages. Thus, the accurate reconstruction of a child's genome is associated with considerable uncertainty. Yet despite this difficulty, being able to reconstruct the child's genome is exactly what is required to be able to predict successfully a risk to the child of inheriting, or acquiring de novo, a genetic disorder.

Known approaches to try to address this challenge of reconstructing a given child's genetic profile have focused on a combination of a rules-based approach, combined with statistical techniques to determine on a per variant basis whether or not a variant call is:

(a) real; and (b) of fetal (foetal) origin.

These approaches use knowledge of parental genotypes, to assess a likelihood of a given observed allele frequency, given a read depth that is achieved at that locus, and to make some decision on whether or not to accept or reject this call.

Relative Haplotype Dosage (RHDO) analysis has been used in a situation where a given father is homozygous for a site and a corresponding given mother is heterozygous (Lam et al., 2012). RHDO analysis is performed on a per locus basis, and involves determining whether or not the number of sequenced reads in respect of the two alleles favours one allele or another (Chiu et al., 2008; Lo et al., 2010). Such a favouring is determined by whether or not there is balance or imbalance in the proportions of reads in respect of a particular allele. If a given child were heterozygous, it would be expected to observe allelic balance, as the given child would have the exact same ratio as the mother in whose blood the reads occur (New et al., 2014; Xiong et al., 2015). However, if the child were homozygous for a given allele, then it would be expected that this data would represent itself as an allelic imbalance, with a large proportion of reads favouring a given site (Xiong et al., 2015). The expectation of the degree of imbalance is dependent upon the fetal (foetal) fraction. From a prediction of allelic balance or imbalance, the given child's genotype at a given site can then be scored. Such an analysis is carried out in a step-wise manner for each variant on a chromosome from those occurring near a start of the chromosome to those occurring near an end of the chromosome in the order they occur (Lam et al., 2012).

More recently, Hidden Markov models (HMM) have also been used to deal with a potential for one or more de novo mutations at any given site. In such a case, maternal inheritance of the foetus is inferred by HMM. Classically, a HMM has three parameters: a latent state, an emission probability and a transition probability. In such an approach using HMM, the allele inherited from the mother is determined from two factors:
 (i) the maternal inheritance of a previous variant in order along the chromosome (latent state) and;
 (ii) the SNP type (emission probability) (Kitzman et al., 2012).

There is therefore employed a model that also accounts for natural haplotype switching events such as genetic recombination (namely transition probability). A proprietary Viterbi™ algorithm employs a recursive algorithm that searches for a given sequence with a maximum associated probability; the proprietary Viterbi™ algorithm is susceptible to being used to generate a most probable latent state sequence (Chan and Jiang, 2015). Altogether, the maternal inheritance of the fetus (foetus) is susceptible to being deduced. A similar method has be used for estimation of paternal inheritance of the foetus (Chan et al., 2016).

In addition, Chan et al, 2016 have used a high coverage base filter method, whereby there is determined a likelihood that each individual base has been called (namely is identified) accurately, using a strict threshold for the number of times a base must have been observed before it is accepted as a 'true' call. This method filters out much of the erroneous variation allowing for a much more confident estimation of real from non-real variance, but requires incredibly high sequence depth for this method to be tenable (Chan et al., 2016); achieving a high sequence depth is both costly and time-consuming to achieve. By this method, in combination with those described above, they were able to recapture a large proportion of the variants in the child that had occurred de novo.

In order to filter at the level of the variant, a dynamic cut off range has been used in order to attempt to identify de novo variations. Such a method was developed to distinguish between de novo mutations present in the foetus and sequencing errors, wherein such distinguishing is achieved by calculating a probability of a same given variant being observed as many times as a current variant purely due to sequencing error and applying a cut off relative to this probability (Chan et al., 2016).

As aforementioned, a child's genetics must be recapitulated (reconstructed) from small fragments of circulating DNA that occur as only a small sub-population of the cell-free DNA present in the mother's plasma, which is itself at relatively low concentrations in a maternal blood sample. Coupled with this small sub-population, next generation sequencing library preparation methods for analysing this cell-free DNA material requires PCR amplification. PCR amplification introduces errors into a given sample being thereby amplified, wherein a frequency of the errors can be greater than a total number of foetal reads within the sample, resulting in a true variation in a given fetal genome being obscured or false positives obtained; such errors are a major technical problem that the present disclosure seeks to address. Even for techniques involving PCR-free approaches, the final sequencing step requires copies of the original DNA molecule to be made, which can also introduce errors. Such sources of error are particularly relevant when trying to identify aforementioned 'de novo' variants which have occurred in a given fetus.

In order to account for these significant (namely, 'not insignificant') sources of error, it is important that identified genetic variants are required to pass extremely stringent quality thresholds, that are employed in methods employed when implementing aforementioned NIPT and associated analyses. When investigating variants across large tracks (portions) of the genome, it is potentially required to employ unconventionally high sequencing depths in order to achieve a cell-free DNA readout, and thus as a by-product foetal DNA readout, achieve at a coverage level that is tractable with such analyses. These very high sequencing depth methods, while being very informative in terms of what can be achieved by NGPS, are generally impractical (namely, too costly and too slow) to implement in a contemporary clinical setting providing NIPT to a general public.

Reducing the technical limitations surrounding NGPS is an area of great importance. The development of methods of (for) handling sources of error, or empowering analysis by targeting investigations towards one or more likely genes of interest, is potentially susceptible to improving an ability to screen accurately for disease-causing mutations using realistic sequence depths when reading collected DNA samples. Thus, a functionality to collect and synthesise information pertinent to analyses, and moreover to learn from earlier analyses that have been performed, is susceptible to improving a utility and an effectiveness of NGPS.

Current approaches attempt to reduce error through the use of one or more thresholds, set at a value relative to the probability of mutational change in the genome (New et al., 2014). Such use of one or more thresholds provides a base filter method requiring a very high coverage of a majority of genetic nucleic acid base sites, whereby the likelihood that each individual base has been called accurately is determined, using a strict threshold for a number of times a base must have been observed before it is accepted as a 'true' call (Yu et al., 2014). Such a method filters out much of the erroneous variation, thereby allowing a much more confident estimation of real from non-real variance to be computed but requires an incredibly high sequence depth for this method to be tenable for practical use in a clinical environment delivering a service to the public.

In order to filter at the level of the variant (for example, giving rise to a genetic abnormality), a dynamic cut off range has been earlier used in order to attempt to identify one or more 'de novo' variations (Chan et al., 2016). Thus, a method has been developed to distinguish between 'de novo' mutations present in a given fetus (foetus) and sequencing errors. Such distinguishing is achieved by calculating a probability of a same given variant being observed as many times as a current variant purely due to sequencing error and applying a cut off relative to this probability (Chan et al., 2016; Yu et al., 2014); as such, the distinguishing is achieved by taking a plurality of sequencing reads and performing a correlation therebetween to remove stochastic noise, and to reinforce systematic variations that are indicative of genetic problems.

Other known methods attempt to improve confidence in DNA nucleic acid base reads being analysed by using a property that, reads derived from circulating cell-free DNA are far more likely to 'stack' at positions in the genome than non-cell free DNA (Chan et al., 2016), sharing both their start and end positions with other read; such stacking arises, for example, on account of apoptotic processes that occur within the fetus during fetal growth. Such a property of 'stacking' is important, because current quality assurance methods in genetic pipelines are designed to remove reads that share the same start and end position as they are assumed to come from PCR duplication of the same read (Chandrananda et al., 2015).

To address erroneous artefacts that are PCR duplicates, analysis protocols typically remove duplicate reads based upon an assumption that two reads with a same given start and a same given end position have arisen from the PCR process, as opposed to being unique DNA molecules; such an assumption is essentially a form of correlation with a purpose of reducing stochastic noise when making measurements. The number of PCR duplicates required tends to increase with lower (namely, smaller) starting amounts of DNA (as is the case with cfDNA). However, it has been determined that unique molecules of cfDNA and cffDNA can have a same start and a same end point, due to preferences of where DNA is sheared, based upon open chromatin regions. This means that by applying a PCR duplicate removal step, 14% of genuine DNA fragments are being discarded (Chan et al., 2016). Thus, such a 'correlation' approach is not without its own problems and inaccuracies.

A technical problem that the present disclosure seeks to address is how to identify unique DNA molecules, wherein the DNA molecules have a mutually same start position and a mutually same end position.

A solution that exists to identify unique DNA molecules is molecular barcoding (MBC); also known as Unique Molecular Indices (UMI). UMI's enable reads to be identified that have arisen as a result of sequencing error. This means PCR artefacts can be removed and real variants kept; for example, a genuine mosaic variant may be discarded due to low allele frequency being encountered.

Molecular barcoding of individual DNA molecules can be used to increase a confidence in a given variant calling, when an expected frequency of mutant reads is at or below an error rate threshold of a DNA nucleic acid base sequencing method. Moreover, each original DNA fragment in a given sample, when implementing the method, is attached to a unique barcode, or unique molecular index (UMI). This UMI is typically a string of random nucleotides, degenerate nucleotides or defined nucleotides. Reads which contain a sequencing error can be removed from downstream analysis while processing various DNA fragment reads. Such a barcoding approach can account for PCR and DNA sequencing errors, and may potentially improve a detection of low allele frequency variants. Based upon this sequencing method using barcodes, the method is potentially susceptible to being used to identify which DNA fragments with mutually identical start and end points are genuine, and which DNA fragments are biological duplicates, and therefore which can be retained for use in further analysis.

Known types of molecular barcoding include incorporation into sequencing adapters during library construction (duplex sequencing) (for example, Peng, Vijaya Satya, Lewis, Randad, & Wang, 2015); and smMIP (single molecule molecular inversion probes), wherein a method employs single-molecule tagging combined with multiplex targeted capture. Specifically, Hiatt, Pritchard, Salipante, O'Roak, & Shendure, (2013) first described this method, wherein 1312 smMIP oligos targeting coding sequences of 33 genes (approx. 125 kb) were designed. Furthermore, publications describing smMIP include, a published US patent application US2016/0055293A describing such a method, systems implementing the method, and algorithms and software for MIP design associated with the method; a BRCA kit available using method; a published US patent application US2016/0055293A describing such a method, systems implementing the method, and algorithms and software for MIP design associated with the method. Additionally, smMIP for non-invasive prenatal diagnosis (NIPD) is being developed at Maastricht University and Radbound UMC. Such an approach appears presently to be on a single gene basis, rather than a panel of genes. Furthermore, it has been suggested that such an approach is a most favoured option for development as combined barcoding and enrichment, wherein there is focus upon a scalability of target regions.

Known commercially-available customizable methods of (for) providing molecular barcodes include Agilent HaloPlex$^{HS}$; Agilent whitepaper on molecular barcoding; QiaSeq Targeted DNA Panel and ArcherDX® Archer MBC Adapters; these names include trade marks (US: trademarks) ®™.

Molecules are labelled with a unique sequence prior to performing PCR amplification. There is employed an adapter that contains a sample-specific index of pre-defined sequences and a random 8-mer molecular barcode (or UMI). This random 8-mer molecular barcode is ligated to fragmented gDNA before amplification. The random 8-mer, along with a random start site generated during the enzymatic shearing, is used to identify duplicates. The cfDNA samples that are of interest, in respect of technology described in the present disclosure, is not subjected to experimental enzymatic fragmentation, but by natural enzymatic processes.

Contemporary aforementioned methods that are currently available for molecular barcoding are restricted to a relatively small number of regions of interest in a DNA molecule via PCR amplicon approaches, meaning that associated DNA analysis has to be very targeted in order to achieve useful DNA sequence readout results.

Therefore, in light of the foregoing discussion, there exist problems associated with conventional pre-natal screening systems.

SUMMARY

The present disclosure seeks to provide an improved prenatal screening system that is capable of providing a non-invasive prenatal screening method, with a lower occurrence of false-positive and false-negatives, in comparison to known pre-natal screening tests, when the system prenatal screening system is employed for providing a prenatal screening service.

Moreover, the present disclosure seeks to provide an improved method of (for) using a prenatal screening system that is capable of providing a lower occurrence of false-positive and false-negatives, in comparison to known pre-natal screening tests, when the system prenatal screening system is employed for providing a prenatal screening service.

In a first aspect, embodiments of the present disclosure provide a prenatal screening system including a wet-laboratory arrangement and a data processing arrangement that exchanges in operation instructions and data with the wet-laboratory arrangement, wherein the data processing arrangement includes a database arrangement in which there is stored genetic information accessible to one or more algorithms executable on the data processing arrangement, wherein the wet-laboratory arrangement is used in operation to collect one or more maternal blood samples from a pregnant mother, characterized in that:

(i) the wet-laboratory arrangement isolates in operation free fetal DNA (ffDNA) fragments present in cell-free DNA (cfDNA) derived from plasma of the one or more maternal blood samples, wherein the isolation utilizes baits based upon coordinates of cell-free fetal DNA (cffDNA) fragment specific end-points; and (ii) the data processing arrangement analyses in operation the isolated free fetal DNA (ffDNA) and compares with one or more DNA templates stored in the data processing arrangement for determining an occurrence of one or more biological characteristics of fetal DNA present in the one or more maternal blood samples.

The present disclosure is of advantage in that it provides an improved personalized non-invasive system and method of (for) identifying genetic abnormalities in a fetus. Moreover, the system disclosed herein is advantageous as it provides no increased risk of miscarriage and has a higher accuracy with false negative and false positive results reduction.

Embodiments of the disclosure are advantageous in terms of providing a rapid, simple, patient-specific and highly efficient method and system for performing prenatal screening. Moreover, the method and system are helpful in making possible prenatal screening at an earlier time in pregnancy than hitherto feasible, and also reducing diagnosis time. Furthermore, the aforementioned method is advantageous in terms of efficient screening of a large number of genes (such as whole exome).

Optionally, the wet-laboratory arrangement enriches in operation the free fetal DNA fragments for providing a plurality of copies of the free fetal DNA fragments for analysis. More optionally, the wet-laboratory arrangement enriches in operation the free fetal DNA fragments by using nucleosome profile to determine the most likely start position and the fetal specific end positions.

Optionally, the baits are designed to avoid maternal DNA present in the plasma. More optionally, the designed baits are in combination with targeting of genes, wherein the genes are relevant to monogenic clinical disorders.

Optionally, the wet-laboratory arrangement isolates and analyses in operation cfDNA fragments in the plasma that start within a nucleosome, wherein the cfDNA fragments correspond to a fetal fraction of the plasma of the one or more maternal blood samples, wherein the cfDNA fragments that start within a nucleosome are relatively shorter in nucleic acid base count than an average length in nucleic acid base count of cfDNA fragments present in the one or more maternal blood samples.

Optionally, the wet-laboratory arrangement performs in operation a combined test for prenatal screening of fetal chromosomal abnormalities, wherein the test includes:

(i) at least one maternal blood test; and/or
(ii) an ultrasound scan of a fetus.

For example, both at least one maternal blood test and an ultrasound scan of a fetus are utilized.

Optionally, the data processing arrangement stores in operation genetic information extracted from the one or more maternal blood samples in a secondary database.

In a second aspect, embodiments of the present disclosure provide a method of (for) using a prenatal screening system including a wet-laboratory arrangement and a data processing arrangement to exchange instructions and data with the wet-laboratory arrangement, wherein the data processing arrangement includes a database arrangement in which there is stored genetic information accessible to one or more algorithms executable on the data processing arrangement, characterized in that the method includes:

(i) using the wet-laboratory arrangement to collect one or more maternal blood samples from a pregnant mother;

(ii) using the wet-laboratory arrangement to isolate free fetal DNA (ffDNA) fragments present in cell-free DNA (cfDNA) derived from plasma of the one or more maternal blood samples, wherein the isolation utilizes baits based upon coordinates of cell-free fetal DNA (cffDNA) fragment specific end-points; and (iii) using the data processing arrangement to analyse the isolated free fetal DNA (ffDNA) and compare with one or more DNA templates stored in the data processing arrangement for determining an occurrence of one or more biological characteristics of fetal DNA present in the one or more maternal blood samples.

Optionally, the method includes using the wet-laboratory arrangement to enrich the free fetal DNA fragments for providing a plurality of copies of the free fetal DNA fragments for analysis. More optionally, the method includes enriching the free fetal DNA fragments by using one or more nucleosome profiles to determine the most likely fetal specific end positions.

Optionally, the method includes designing the baits to enrich fetal DNA present in the cfDNA. More optionally, the designed baits are employed in combination with targeting of genes, wherein the genes are relevant to monogenic clinical disorders.

Optionally, that the method includes using the wet-laboratory arrangement to isolate and analyse cfDNA fragments in the plasma that start within a nucleosome, wherein the cfDNA fragments correspond to a fetal fraction of the plasma of the one or more maternal blood samples, wherein the cfDNA fragments that start within a nucleosome are relatively shorter in nucleic acid base count than an average length in nucleic acid base count of cfDNA fragments present in the one or more maternal blood samples.

Optionally, the method includes using the wet-laboratory arrangement to perform a combined test for prenatal screening of fetal chromosomal abnormalities, wherein the combined test includes:

(i) at least one maternal blood test; and/or
(ii) an ultrasound scan of a fetus.

For example, both at least one maternal blood test and an ultrasound scan of a fetus are employed.

Optionally, the method includes using the data processing arrangement to store genetic information extracted from the maternal blood samples in a secondary database. For example, the secondary database is implemented to include a knowledgebase, a curated variant/gene list.

In a third aspect, embodiments of the present disclosure provide a screening system that, when in operation:

(i) processes a biological sample in a wet-laboratory arrangement to determine a presence of cell-free DNA (cfDNA) fragments therein, to sequence the DNA fragments; and (ii) uses a data processing arrangement to compare information representative of the sequenced DNA fragments against information stored in a genomic database arrangement to provide an assessment score in respect of the biological sample, characterized in that the screening system applies in operation a modification to one or more stochastic ratings associated with the information representative of the sequenced DNA fragments using secondary information provided to the screening system to reduce a stochastic and/or systemic uncertainty present in the assessment score.

Optionally, the screening system distinguishes in operation between cell-free DNA fragments of maternal origin and cell-free DNA fragments of placental and/or fetal origin.

Optionally, the screening system employs in operation at least one of following scores when computing the modification in the data processing arrangement:
  (a) a genome locality score, wherein the genome locality score includes a likelihood of a mutation within a region;
  (b) a sequence error score, wherein the sequence error score includes a likelihood of a given nucleic acid base being a result of PCR infidelity during template amplification and/or a miscall during a sequencing process;
  (c) a patient modifier score, wherein the patient modifier score includes details from external sources such as clinical phenotype; and
  (d) a mosaicism detection score, wherein the mosaicism detection score includes a likelihood of variants occurring in a region of imbalanced maternal genotype.

Optionally, the likelihood of mutation within the region is calculated on a basis of frequencies of change susceptible to occur to the region and/or frequencies of calling spurious variants in the region.

Optionally, the sequence error score is calculated using a maternal genetic sequence.

Optionally, the information for external sources includes at least information received from ultrasound scans.

Optionally, the screening system converts in operation the genome locality score into a weight for a particular locus.

Optionally, the screening system applies in operation the sequence error score as a weight and to modify confidence in a base call.

Optionally, the screening system converts in operation the details from external sources in to a weight.

Optionally, the screening system combines in operation the genome locality score, the sequence error score, the patient modifier score and/or mosaicism detection score to modify the confidence of a call.

Optionally, the screening system in operation uses the biological sample containing cfDNA fragments therein that is extracted from a pregnant woman in a non-invasive manner.

In a fourth aspect, embodiments of the present disclosure provide a method of (for) using a screening system that in operation:
  (i) processes a biological sample in a wet-laboratory arrangement to determine a presence of cell-free DNA (cfDNA) fragments therein, to sequence the DNA fragments; and
  (ii) uses a data processing arrangement to compare information representative of the sequenced DNA fragments against information stored in a genomic database arrangement to provide an assessment score in respect of the biological sample, characterized in that the method includes operating the screening system to apply a modification to one or more stochastic ratings associated with the information representative of the sequenced DNA fragments using secondary information provided to the screening system to reduce a stochastic and/or systemic uncertainty present in the assessment score.

Optionally, the method includes distinguishing between cell-free DNA fragments of maternal original from cell-free DNA fragments of placental and/or fetal origin.

Optionally, the method includes employing at least one of following scores when computing the modification in the data processing arrangement:
  (a) a genome locality score, wherein the genome locality score includes a likelihood of a mutation within a region;
  (b) a sequence error score, wherein the sequence error score includes a likelihood of a given nucleic acid base is a result of PCR infidelity during template amplification and/or a miscall during the sequencing process;
  (c) a patient modifier score, wherein the patient modifier score includes details from external sources; and
  (d) a mosaicism detection score, wherein the mosaicism detection score includes a likelihood of variants occurring in a region of imbalanced maternal genotype.

Optionally, the method includes calculating the likelihood of mutation within the region on the basis of frequencies of change is to occur to the region and/or frequencies of calling spurious variants in the region.

Optionally, the method includes calculating the sequence error score using maternal genetic sequence.

Optionally, the method includes receiving information from ultrasound and magnetic resonance imaging (MRI) scans.

Optionally, the method includes converting the genome locality score into a weight for a particular locus.

Optionally, the method includes applying the sequence error score as a weight and to modify confidence in a base call.

Optionally, the method includes converting the details from external sources in to a weight.

Optionally, the method includes combining the genome locality score, the sequence error score, the patient modifier score and/or mosaicism detection score to modify the confidence of a call.

Optionally, the method includes extracting the biological sample containing cfDNA fragments therein from a pregnant woman in a non-invasive manner.

In a fifth aspect, embodiments of the present disclosure provide a prenatal screening system, wherein the prenatal screening system includes a wet-laboratory arrangement for processing a blood sample to determine cell-free DNA readout data from the blood sample, and a data processing arrangement for processing the cell-free DNA readout data with reference to information stored in a database arrangement to generate a risk score indicative of whether or not there are genetic abnormalities in the blood sample that are indicative of fetal abnormalities, characterized in that the prenatal screening system uses in operation secondary data describing a donor of the blood sample for modifying data processing performed in the data processing arrangement for processing selective regions of the cell-free DNA readout data when generating the risk score.

Optionally, the blood sample is a maternal blood sample, and the cell-free DNA readout data is determined from fragments of DNA present in a plasma fraction of the blood sample. More optionally, the wet-laboratory arrangement amplifies in operation the fragments of DNA to provide amplified DNA for nucleic acid base sequencing or readout to generate the cell-free DNA readout data.

Optionally, the selective regions are determined by accessing one or more databases of the database arrangement, wherein the prenatal screening system updates in operation the one or more databases recursively or iteratively depending upon a determined accuracy of the risk score to one or more subsequent fetal investigations. More optionally, the secondary data is determined by non-invasive procedures, and the subsequent fetal investigation involves executing one or more invasive sampling of tissue or liquids in respect of the fetus.

Optionally, the one or more database are implemented as a NGPS knowledgebase, wherein the NGPS knowledgebase includes analyses that are recalibrated in operation to include and incorporate information that is specific to a donor of the blood sample. More optionally, the NGPS knowledgebase includes phenotypic information that is employed in analyses of data performed by the data processing arrangement when generating the risk score.

In a sixth aspect, embodiments of the present disclosure provide a method of (for) using a prenatal screening system, wherein the prenatal screening system includes a wet-laboratory arrangement for processing a blood sample to determine cell-free DNA readout data from the blood sample, and a data processing arrangement for processing the cell-free DNA readout data with reference to information stored in a database arrangement to generate a risk score indicative of whether or not there are genetic abnormalities in the blood sample that are indicative of fetal abnormalities, characterized in that the method includes operating the prenatal screening system to use secondary data describing a donor of the blood sample for modifying data processing performed in the data processing arrangement for processing selective regions of the cell-free DNA readout data when generating the risk score.

Optionally, the blood sample is a maternal blood sample, and the method includes determining the cell-free DNA readout data from fragments of DNA present in a plasma fraction of the blood sample. More optionally, the method includes operating the wet-laboratory arrangement to amplify the fragments of DNA to provide amplified DNA for nucleic acid base sequencing or readout to generate the cell-free DNA readout data.

Optionally, the method includes determining the selective regions by accessing one or more databases of the database arrangement, wherein the prenatal screening system updates in operation the one or more databases recursively or iteratively depending upon a determined accuracy of the risk score to one or more subsequent fetal investigations. More optionally, the method includes determining the secondary data by non-invasive procedures, and determining the subsequent fetal investigation by executing one or more invasive sampling of tissue or liquids in respect of the fetus.

Optionally, the method includes implementing the one or more databases as a NGPS knowledgebase, wherein the NGPS knowledgebase includes analyses that are recalibrated in operation to include and incorporate information that is specific to a donor of the blood sample. More optionally, the method includes arranging for the NGPS knowledgebase to include phenotypic information that is employed in analyses of data performed by the data processing arrangement when generating the risk score.

In a seventh aspect, embodiments of the present disclosure provide a prenatal screening system, wherein the prenatal screening system includes a wet-laboratory arrangement for processing a blood sample to determine cell-free DNA readout data from the blood sample, and a data processing arrangement for processing the cell-free DNA readout data with reference to information stored in a database arrangement to generate a risk score indicative of whether or not there are genetic abnormalities in the blood sample that are indicative of fetal abnormalities, characterized in that the prenatal screening system ligates in operation nucleic acid base molecular barcodes to fragments of the cell-free DNA present in the blood sample prior to amplifying the molecular barcode-ligated DNA fragments for sequencing the amplified molecular barcode-ligated fragments to generate the cell-free DNA readout data.

Optionally, the prenatal screening system implements in operation the molecular barcode (UMI) as an n-mer, wherein n is in a range of 3 to 100. More optionally, the n is in a range of 4 to 20. Moreover optionally, the n is 10.

Optionally, the molecular barcode (UMI) includes a random sequence of nucleic acid bases.

Optionally, the wet-laboratory arrangement incorporates in operation the molecular barcode (UMI) to a cell-free DNA library containing a fetal component, and uses the cell-free DNA library thereby obtained in hybridisation-based enrichment for identifying de novo variants when computing the risk score.

Optionally, the prenatal screening system ligates in operation nucleic acid base molecular barcodes to the fragments to generate corresponding barcoded fragments, and performs enrichment by hybridization using baits targeted at genes that are susceptible to causing fetal illnesses.

Optionally, the prenatal screening system performs in operation non-invasive molecular diagnosis of a fetus which on ultrasound investigation presents with a skeletal abnormality and/or a cardiac abnormality.

In an eighth aspect, embodiments of the present disclosure provide a method of (for) using a prenatal screening system, wherein the prenatal screening system includes a wet-laboratory arrangement for processing a blood sample to determine cell-free DNA readout data from the blood sample, and a data processing arrangement for processing the cell-free DNA readout data with reference to information stored in a database arrangement to generate a risk score indicative of whether or not there are genetic abnormalities in the blood sample that are indicative of fetal abnormalities, characterized in that the method includes:

(i) ligating nucleic acid base molecular barcodes to fragments of the cell-free DNA present in the blood sample;
  (ii) amplifying the molecular barcode-ligated fragments; and
  (iii) sequencing the amplified molecular barcode-ligated fragments to generate the cell-free DNA readout data.

Optionally, the method includes operating the prenatal screening system to implement the molecular barcode (UMI) as an n-mer, wherein n is in a range 3 to 100. More optionally, the n is in a range of 4 to 20. Moreover optionally, the n is 10.

Optionally, the method includes arranging for the molecular barcode to include a random sequence of nucleic acid bases.

Optionally, the method includes operating the wet-laboratory arrangement to incorporate the molecular barcode to a cell-free DNA library containing a fetal component, and to use the cell-free DNA library thereby obtained in hybridisation-based enrichment for identifying de novo variants when computing the risk score.

Optionally, the method includes operating the prenatal screening system to generate the cell-free DNA fragments by employing enzymic digestion, to ligate nucleic acid base molecular barcodes to the fragments to generate corresponding barcoded fragments, and to perform enrichment by hybridization using baits targeted at genes which for one or more diseases that are susceptible to causing fetal illnesses.

Optionally, the method includes operating the prenatal screening system to perform non-invasive molecular diagnosis of a fetus which on ultrasound presents with a structural abnormal, for example skeletal abnormality, cardiac abnormality. More optionally, the abnormality is caused by a de novo mutation.

In a ninth aspect, embodiments of the present disclosure provide a computer program product comprising a non-transitory computer-readable storage medium having computer-readable instructions stored thereon, the computer-readable instructions being executable by a computerized device comprising processing hardware to execute one or more the aforementioned methods, for example one of the methods, for example a plurality of the methods used in combination.

In a tenth aspect, embodiments of the present disclosure provide a screening system, characterized in that the screening system includes a combination of at least two of the screening system of the first aspect, the screening system of the third aspect, the screening system of the fifth aspect, and the screening system of the seventh aspect. Optionally, the screening system includes a combination of all of the screening systems of the first aspect, the screening system of the third aspect, the screening system of the fifth aspect and the screening system of the seventh aspect.

Another aspect of the invention, there is provided a product comprising a wet laboratory kit and a data processing database system. Optionally, the data processing database system is an arrangement that allows access to a data processing database defined according to the previous aspects of the disclosure. Optionally, the wet laboratory kit is a wet laboratory arrangement as defined in aspects one to ten of the present disclosure.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

A better understanding of the present invention may be obtained through the following examples which are set forth to illustrate but are not to be construed as limiting the present invention.

BRIEF DESCRIPTION OF DRAWINGS

Embodiments of the present disclosure will be more fully understood from examples described hereinafter and the accompanying drawings, which are given by way of illustration only, and are thus not limitative of the present invention, and wherein.

Figure 1:
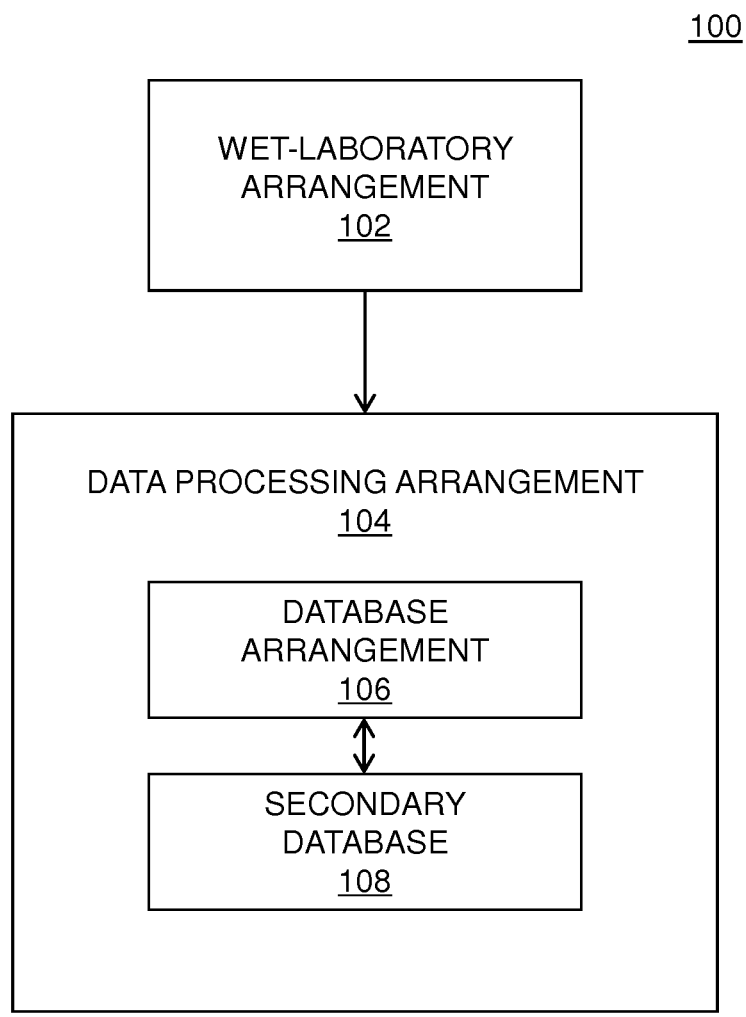
FIG. 1 is a schematic illustration of a prenatal screening system, in accordance with an embodiment of the present disclosure.

In the accompanying diagrams, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

| LIST OF ABBREVIATIONS | |
|---|---|
| Abbreviation | Meaning |
| RMD | Relative Mutation Dosage |
| RHDO | Relative Haplotype Dosage |
| PCR | Polymerase Chain Reaction |
| NT | Nuchal Translucency |
| cffDNA | Cell-Free Fetal DNA |
| NIPT | Non-Invasive Prenatal Testing |
| cfDNA | Cell-Free DNA |
| NGPS | Next Generation Prenatal Screening |

Definitions

As used herein, the following terms shall have the following meanings:

As used herein, the term 'data processing arrangement' refers to a process and/or system that can be embodied in software that determines, when in operation, the biological significance of acquired data (i.e., the ultimate results of an assay). For example, a data processing arrangement can determine the amount of each nucleotide sequence species based upon the data collected. A data processing arrangement may also control an instrument and/or a data collection system based upon results determined. A data processing and a data collection arrangement often are integrated and provide feedback to operate data acquisition by the instrument, and hence provide assay-based judging methods provided herein.

As used herein, the term 'database arrangement' refers to a nucleic acid database known in the art including, for example, GenBank®, dbEST®, dbSTS®, EMBL® (European Molecular Biology Laboratory), ClinVar, gnomAD and DDBJ® (DNA Databank of Japan). BLAST® or similar tools can be used to search the identified sequences against a sequence database.

As used herein, the term 'cell-free DNA' refers to DNA that is not within a cell. In one embodiment, cell free DNA includes DNA circulating in blood. In another embodiment, cell free DNA includes DNA existing outside a cell. In yet another embodiment, cell free DNA includes DNA existing outside a cell as well as DNA present in a blood sample after such blood sample has undergone partial or gentle cell lysing.

As used herein, 'polymerase chain reaction (PCR)' is a technique used in molecular biology to amplify a single copy or a few copies of a segment of DNA by several orders of magnitude, thereby generating potentially thousands of millions of copies of a particular given DNA sequence.

As used herein, 'bridge amplification' or 'amplification' is employed in massively parallel sequencing for DNA sequencing purposes using a concept of massively parallel processing, wherein use is made of miniaturized and parallelized platforms for sequencing in a range of 1 million to 43 billion short reads (50 to 400 nucleic acid bases each) per instrument run.

As used herein, 'zygosity' refers to a degree of similarity of alleles for a trait in a given organism, for example a given fetus.

As used herein, the term 'genetic information' refers to information related to nucleic acids, altered nucleotide sequence, chromosomes, segments of chromosomes, polymorphic regions, translocated regions, the like or combinations of the foregoing. Furthermore, the nucleic acids may include, are but not limited to, DNA, cDNA, RNA, mRNA, t RNA and rRNA. Moreover the genetic information may include information related to mutations, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, abnormal changes in nucleic acid methylation infection or cancer.

As used herein, the term 'free fetal DNA' refers to DNA that originates from a given fetus and not a mother of the given fetus, wherein the DNA is not within a cell. In one embodiment, cell free fetal DNA includes fetal DNA circulating in maternal blood. In another embodiment, cell free fetal DNA includes fetal DNA existing outside a cell, for example outside a fetal cell. In yet another embodiment, cell free fetal DNA includes fetal DNA existing outside a cell as well as fetal DNA present in maternal blood sample after such blood sample has undergone partial or gentle cell lysing. Herein, the term 'free fetal DNA' also refers to small DNA fragments (i.e. about <300 base pairs) circulating in maternal plasma; in other terms, it is the excluding DNA contained in fetal cells that may circulate in the maternal plasma.

As used herein, the terms 'maternal sample' or 'maternal blood sample' refers to the sample obtained from a female who is pregnant, the sample may include, but is not limited to, plasma, serum, peripheral blood and urine. Typically, the sample is a maternal plasma sample, although other tissue sources that contain both maternal and fetal DNA can be used. Maternal plasma can be obtained from a peripheral whole blood sample from a pregnant woman and the plasma can be obtained by standard methods. A volume of 3 ml to 5 ml of plasma is sufficient to provide suitable DNA material for analysis. The cell free DNA can be extracted from the sample using standard techniques, non-limiting examples of which include a Qiasymphony® protocol (Qiagen®) suitable for free fetal DNA isolation or any other automated or manual extraction method suitable for cell free DNA isolation.

As used herein, the term 'biological characteristics' refers to the genetic variations, abnormalities, irregularities or mutations which range extensively from changes in single nucleotides to the presence of additional whole chromosomes or abnormal number of chromosomes. The chromosomal abnormality is a structural abnormality, including, but not limited to, copy number changes including microdeletions and microduplications, insertions, translocations, inversions and small-size mutations including point mutations and mutational signatures.

As used herein, the term 'wet-laboratory arrangement' refers to a facility, clinic and/or a setup of: instruments, equipment and/or devices used for extraction, collection, processing and/or analysis of body fluid samples; instruments, equipment and/or devices used for extraction, collection, processing and/or analysis of genetic material; instruments, equipment and/or devices used for amplification, enrichment and/or processing of genetic material received from the body fluid samples; instruments, equipment and/or devices used for extraction and/or analysis of the genetic information received from the amplified genetic material. Herein the instruments, equipment and/or devices may include but not limited to centrifuge, ELISA, spectrophotometer, PCR, RT-PCR, High-Throughput-Screening (HTS) system, Microarray system, Ultrasound, genetic analyser, deoxyribonucleic acid (DNA) sequencer and SNP analyser. The wet-laboratory arrangement is used in operation to monitor and/or scan a fetus, for example using ultrasonic scanning apparatus providing animated images of the fetus ("ultrasound scanner"). Herein, the wet-laboratory arrangement may include equipment, instruments and/or devices for scanning the fetus. Such equipment, instruments and/or devices include ultrasound scanners (as aforementioned), presymptomatic genetic testing and/or combined tests.

As used herein, the term "barcode" refers to a unique oligonucleotide sequence that allows a unique nucleic acid fragment to be identified. This unique oligonucleotide sequence may be termed a unique molecular identifier (UMI) or a molecular barcode. In certain aspects, the nucleic acid base and/or nucleic acid sequence is located at a specific position on a larger polynucleotide sequence (for example, a covalently attached polynucleotide to a bead). Oligonucleotides are often short DNA or RNA molecules, oligomers, that have a wide range of applications in genetic testing, research, and forensics. Moreover, such oligonucleotides are commonly made in a laboratory by solid-phase chemical synthesis; these small bits of nucleic acids can be manufactured as single-stranded molecules with potentially any user-specified sequence, and so are vital for artificial gene synthesis, polymerase chain reaction (PCR), DNA sequencing, library construction and as molecular probes. In nature, oligonucleotides are usually found as small RNA molecules that function in the regulation of gene expression (for example, microRNA), or are degradation intermediates derived from the breakdown of larger nucleic acid molecules.

Target enrichment is used to isolate specific fragments of genomic DNA for sequencing. A library of complementary oligonucleotide "baits" is used to retrieve fragments of interest (namely, target DNA). The target DNA hybridizes well with the baits, but other DNA does not, which forms a basis of a powerful selection method that correspond to synthesizing actively parts of the genome rather than the epi-genome that regulates genome expression. As used herein, the term 'baits' refers to bioactive molecules which are used to interact with other bioactive molecules such as genes of interest or target genes. Such baits, when designed, will be employed in combination with the targeting of genes which are relevant to monogenic clinical disorders and for the enrichment of fetal DNA from a maternal plasma sample. The baits are, for example, prepared beforehand, and are optionally selected from a library of prepared baits. Libraries of such baits are provided by commercial organisations, for example based in the USA. Moreover, such libraries include up to, for example, 100000 different types of baits. Beneficially, the baits correspond to active synthesizing parts of the human genome, wherein DNA sequence variation can give rise to illnesses to be detected using systems and methods of the present disclosure; for example, epi-genomic parts of a genome do not provide most suitable baits, because these epi-genomic parts are prone to experience relatively large variations from one individual organism to another.

The baits include a portion of DNA bases (for example 120 bases in sequence, although other numbers of bases are possible, for example in a range of 20 to 200 bases) with a biotin group attached to end of the portion. The biotin group is magnetically polarized, and can be attracted to a magnet moved around in a given liquid; such a technique enables a spatial concentration of cfDNA fragments to be achieved in wet laboratory apparatus.

When processing a sample of maternal blood, the baits are added to the cfDNA derived from blood plasma, so the baits (with their biotin groups) bind to corresponding fragments of cfDNA in, attracted baits and associated cfDNA fragments attached are enriched and cfDNA fragments amplified.

The baits are commercially available (for example, from Agilent Biosystems, USA), wherein the baits are available in large libraries that provide a choice of many tens of thousands of different types of baits, for example as aforementioned. Agilent Biosystems, for example, provides a target enrichment library that is, for example, used in embodiments of the present disclosure, to provide a final product containing a set of biotinylated oligonucleotides. However, when the library was is created in eArray® (by Agilent®), the bait sequences are specified in terms of DNA bases (A, C, G, T). The baits are designed to have DNA sequences corresponding to specific groups of DNA bases in a human gene, wherein the specific groups can give rise to various types of illnesses that have fetal health consequences. The baits correspond to active synthesizing parts of the genome rather than the epi-genome that regulates genome expression.

Alternatively, non-commercially available baits may be preferred. These baits may be specifically designed and may be formed of any number of DNA bases, preferably 20 to 300 bases, for example 50 to 200 bases, preferably 100 to 150 bases.

As used herein, the terms 'biological sample' refers to the sample obtained from a female who is pregnant, the sample may include, but is not limited to, plasma, serum, peripheral blood and urine. Typically, the sample is a maternal plasma sample derived from blood, although other tissue sources that contain both maternal and fetal DNA are optionally used. Maternal plasma can be obtained from a peripheral whole blood sample from a pregnant woman and the plasma can be obtained by standard methods. A volume of 3 ml to 5 ml of plasma is sufficient to provide suitable DNA material for analysis. The cell free DNA can be extracted from the sample using standard techniques, non-limiting examples of which include a Qiasymphony® protocol (Qiagen®) suitable for free fetal DNA isolation or any other automated or manual extraction method suitable for cell free DNA isolation.

As used herein, secondary data is data arrived at from inspection of a given mother, for example by using ultrasound scans, collecting data describing a family history of the given mother, lifestyle parameters of the given mother (for example smoker or non-smoker, obesity, alcoholic or non-alcoholic, narcotic substance abuser, a medical history of the given mother (for example, previous infectious disease experienced by the given mother), a medication history of the given mother (for example, treatment, surgery and medicines consumed by the given mother) and so forth. Furthermore, the secondary data can include information describing characteristics of a child being borne by a given mother through pregnancy.

As used herein, the NGPS knowledgebase is a repository for information pertaining to one or more targeted assay approaches including a database to store information regarding a given patient and is composed of a plurality of parts:

(i) a first part P1, concerns construction of a database arrangement, containing information directly relevant to a screening process being performed for the given person, for example for a pregnant mother;

(ii) a second part P2 concerning a genomic capture area database;

(iii) a third part P3 concerning a patient information database; and (iv) a fourth part P4 concerning a sequencing run database.

In addition, the 'NGPS knowledgebase' may include one or more algorithms that useable to update and remodel existing data set information with every new data set of additional information being received.

As used herein, the genomic capture area database is a database that indicates:

(i) a likelihood of erroneous calling in these regions of the genome; and (ii) a likelihood of mutation at the genetic level as well as the known deleterious variants and their associated phenotype (HPO terms).

As used herein, the sequencing information database is a database that includes information about each sample including library preparation quality scores, a degree to which sequencing errors have been observed within the sequence data for sequencing run executed for each sample, an estimated fetal fraction for each sample, and an estimated percentage coverage of the genome by cell-free DNA for each sample to enable both an investigation of patterns in sequencing results obtained, that may not be related to associated underlying genetics, and the potential to learn from challenges due to sequencing technology limitations or artefacts.

DETAILED DESCRIPTION

Practical implementation of the embodiments of the present disclosure are described in further detail below; these embodiments are operable to employ (namely, employ when in operation), unless otherwise indicated, conventional methods of diagnostics, molecular biology, cell biology, biochemistry and immunology within the skill of the art. Such techniques are explained fully in the literature, for example contemporary academic research literature pertaining to pregnancy and genetic material processing. However, it will be appreciated that new combinations of known methods of diagnostics can give rise to new inventions.

It will be appreciated that certain features of the present invention, which are for clarity described in the context of separate embodiments, may also be provided in combination in a single embodiment. Conversely various features of the invention, which are for brevity, described in the context of a single embodiment, may also be provided separately and/or in any suitable sub-combination.

The following detailed description illustrates embodiments of the present disclosure and ways in which they can be implemented. Although some modes of carrying out the present disclosure have been described, those skilled in the art would recognize that other embodiments for carrying out or practicing the present disclosure are also possible.

In FIG. 1, there is shown an illustration of a prenatal screening system 100, in accordance with an embodiment of the present disclosure. The prenatal screening system 100 includes a wet-laboratory arrangement 102 and a data processing arrangement 104. The data processing arrangement 104 is operable to exchange (namely, exchanges, when in operation) instructions and data with the wet-laboratory arrangement 102. The data processing arrangement 104 is operable to access (namely, accesses, when in operation) a database arrangement 106 and a secondary database 108. Furthermore, information stored in the database arrangement 106 is accessible to one or more algorithms executable on the data processing arrangement 104. Herein, the wet-laboratory arrangement 102 is operable to collect (namely, collects, when in operation) one or more maternal blood samples from a pregnant mother, for example a single blood sample or a plurality of blood samples; however, other body fluids (for example, saliva, sputum), for example excretions, are optionally used for providing such samples when non-invasive methods of sample collection are to be employed (for example, for ethical reasons). Moreover, the wet-laboratory arrangement 102 is operable to enrich (namely, enriches when in operation) free fetal DNA (ffDNA) fragments present in cell-free DNA (cfDNA) derived from plasma of the maternal blood sample (or non-invasive samples, as aforementioned). The enrichment of free fetal DNA (ffDNA) utilizes baits based upon coordinates of cell-free fetal DNA (cffDNA) fragment specific end-points, for example specific end-points arising due to cell apoptosis. Furthermore, the data processing arrangement 106 analyses (namely, is operable to analyse) the cell free fetal DNA (cffDNA) and compare them with one or more DNA templates stored in the data processing arrangement 106 for determining an occurrence of one or more biological characteristics of fetal DNA present in the maternal blood samples.

In an embodiment, the wet-laboratory arrangement 102 of the prenatal screening system 100 may be operable to amplify (namely, amplifies when in operation) free fetal DNA fragments for providing a plurality of copies of the free fetal DNA fragments for analysis by the data processing arrangement 104. In this exemplary embodiment, the wet-laboratory arrangement 102 may include a PCR for amplifying the free fetal DNA fragments for providing a plurality of copies of the free fetal DNA to the data processing arrangement 104 for accessing genetic information in the database arrangement 106. In this embodiment, the wet-laboratory arrangement 102 may enrich the free fetal DNA by using nucleosome profiles for determining the fetal specific start and end positions of the free fetal DNA fragments.

In another embodiment, optionally, the prenatal screening system 100, in operation, designs baits, alternatively selects baits from a library of baits, for avoiding contamination arising from maternal DNA present in the plasma extracted from the maternal blood sample; in other words, the baits are employed as a form of biological filter for distinguishing between DNA fragments of fetal origin from those of maternal origin. In this embodiment, the designed baits, alternatively baits selected from a library of baits, may be chosen in combination with the targeted genes. For example, the targeted genes may include, but are not limited to, the genes relevant to monogenic and/or polygenic clinical disorders.

In an embodiment, optionally, the wet-laboratory arrangement 102 isolates and analyses, in operation, cfDNA fragments in the plasma that start within a nucleosome. Moreover, the cfDNA fragments correspond to a fetal fraction of the plasma of the maternal blood sample. In this embodiment, the cfDNA fragments that start within a nucleosome may be relatively shorter in nucleic acid base count than an average length in nucleic acid base count of cfDNA fragments present in the maternal blood sample (for example, ~143 bases long for the fetus relative to ~166 bases long for a corresponding mother)(optionally, for example, the fetal cfDNA fragments are in a range of 135 to 155 bases long, whereas the maternal cfDNA fragments are in a range of 150 to 175 bases long).

In another embodiment, optionally, the wet-laboratory arrangement 102 performs, in operation, a combined test for prenatal screening of fetal chromosomal abnormalities. In this embodiment, the combined test may include, but is not limited to, a maternal blood test and an ultrasound scan of a fetus.

In an example operation of the prenatal screening system 100, a mother with fetus is presented to the prenatal screening system 100. The prenatal screening system 100 is used to perform an ultrasonic scanning test on the fetus to generate an ultrasonic image or video of the fetus, and a cardiac abnormality in the fetus is identified from the ultrasonic test. For example, it is deduced, that there is a risk of the mother suffering a miscarriage of the fetus if an aforementioned invasive amniocentesis or chorionic villus were to be performed. Many mothers, alternatively parents, would in such a situation choose not to pursue such invasive sampling for purposes of performing genetic testing. However, beneficially, the prenatal screening system 100 is capable of providing a non-invasive assay from which it is feasible to make a genetic diagnosis. The non-invasive assay includes enriching a proportion of cell-free fetal DNA (cffDNA) fragments in free fetal DNA (ffDNA) that is derived from a maternal blood sample, wherein the assay includes coordinates of cell-free DNA fragment specific end-points and genes that are relevant to a given disorder under investigation. Information indicative of favoured fetal fragment end positions and nucleosome profiles may be accessed by the prenatal screening system 100 from its database arrangement 106. There are thereby provided, namely 'designed', for the enrichment of fetal DNA from a maternal plasma sample derived from the aforementioned maternal blood sample. The information is, for example, iteratively updated, thereby improving an accuracy and relevance of the information.

In yet another embodiment, the data processing arrangement 104 stores in operation genetic information extracted from the maternal blood samples in a secondary database 108.

Figure 2:
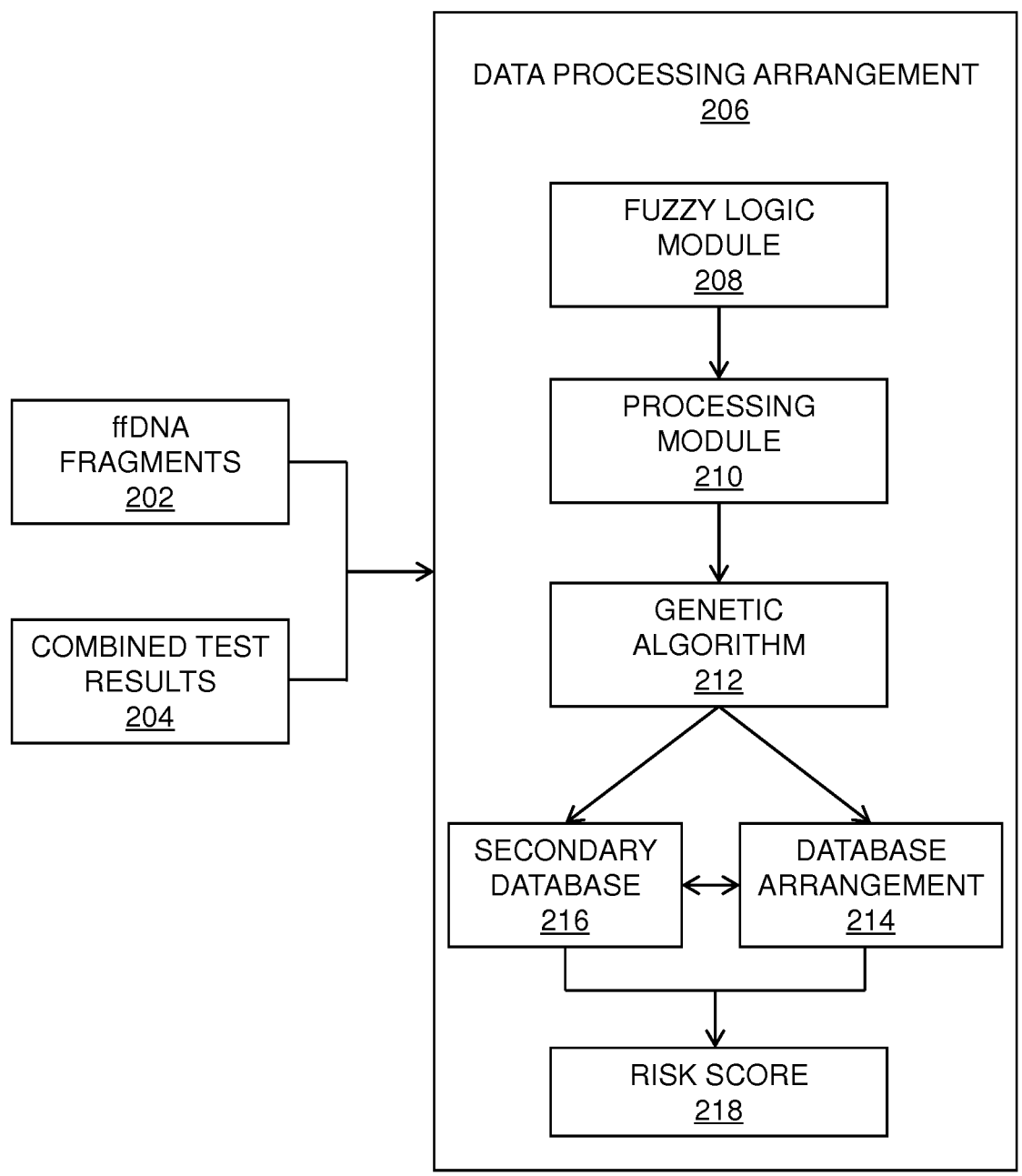
FIG. 2 is a Kalman filter equivalent representation of the system of FIG. 1, in accordance with an embodiment of the present disclosure.

In FIG. 2, there is shown an illustration of a Kalman filter equivalent representation 200 of the system (such as prenatal screening system 100 of FIG. 1), in accordance with an embodiment of the present disclosure. The Kalman filter equivalent representation 200 of the system 100 includes a combined feed of genetic information received from free fetal DNA (ffDNA) fragments 202 and information received for combined test of a fetus 204 to a data processing arrangement 206 (such as data processing arrangement 104 of FIG. 1). The data processing arrangement 206 implements in operation a Kalman filter on the genetic information received from free fetal DNA (ffDNA) fragments 202 and information received for combined test of a fetus 204. The data processing arrangement 206 further includes a fuzzy logic module 208, a processing module 210, a genetic algorithm 212 for matching the cff-DNA fragment in a database arrangement 214 (such as database arrangement 106 of FIG. 1), a secondary database 216 (such as secondary database 108 of FIG. 1) for storing the risk score 218 received from the processing module 210. In this embodiment, the data processing system 206 implements, in operation the Kalman filter on the genetic material received from the maternal blood sample for removing contamination. Furthermore, the genetic algorithm 212 matches when executed in operation upon computing hardware the ffDNA fragments in the database arrangement 214 and, from achieving such matching, computes the risk score 218.

In an exemplary embodiment, the prenatal screening system 100 executes in operation the genetic algorithm 212 in the data processing arrangement 104 for using the information indicative of the favoured fetal fragment end positions and nucleosome profiles. In this embodiment, the maternal plasma sample derived from the aforementioned maternal blood sample includes DNA sequences that are enriched using an assay targeting favoured fetal fragment end-points; such enrichment is achieved, for example, using baits as described in the foregoing. Furthermore, the prenatal screening system 100 uses favoured positions of fetal specific reads derived from nucleosome positioning to enrich in operation fragments of cfDNA. In this embodiment, the processing module 210 validates, in operation, positions of the cffDNA fragments.

In an embodiment, the prenatal screening system 100 differentiates, in operation, maternal and fetal components of cfDNA. In this embodiment, such differentiation may be achieved by employing an assay design which enriches the fetal component and which aids in mapping of maternal and fetal reads.

In an exemplary embodiment, in operation, the prenatal screening system 100 designs and/or selects baits and employs the baits at the fetal-specific positions and fetal-maternally shared positions. Moreover, the bait designs may be made in combination with the targeting of genes which are relevant to monogenic clinical disorders.

In yet another exemplary embodiment, the positioning of the fragments at specific locations is due to non-random fragmentation of DNA, and it has been postulated that plasma DNA fragments are cleaved in accessible parts of the genome. Furthermore, shorter cfDNA fragments start within the nucleosome and it has been shown that these fragments positively correlate with fetal fraction. Moreover, by using the nucleosome profile to determine the most likely start position and the fetal specific end positions, the prenatal screening system 100 may improve the enrichment of cffDNA.

Figure 3:
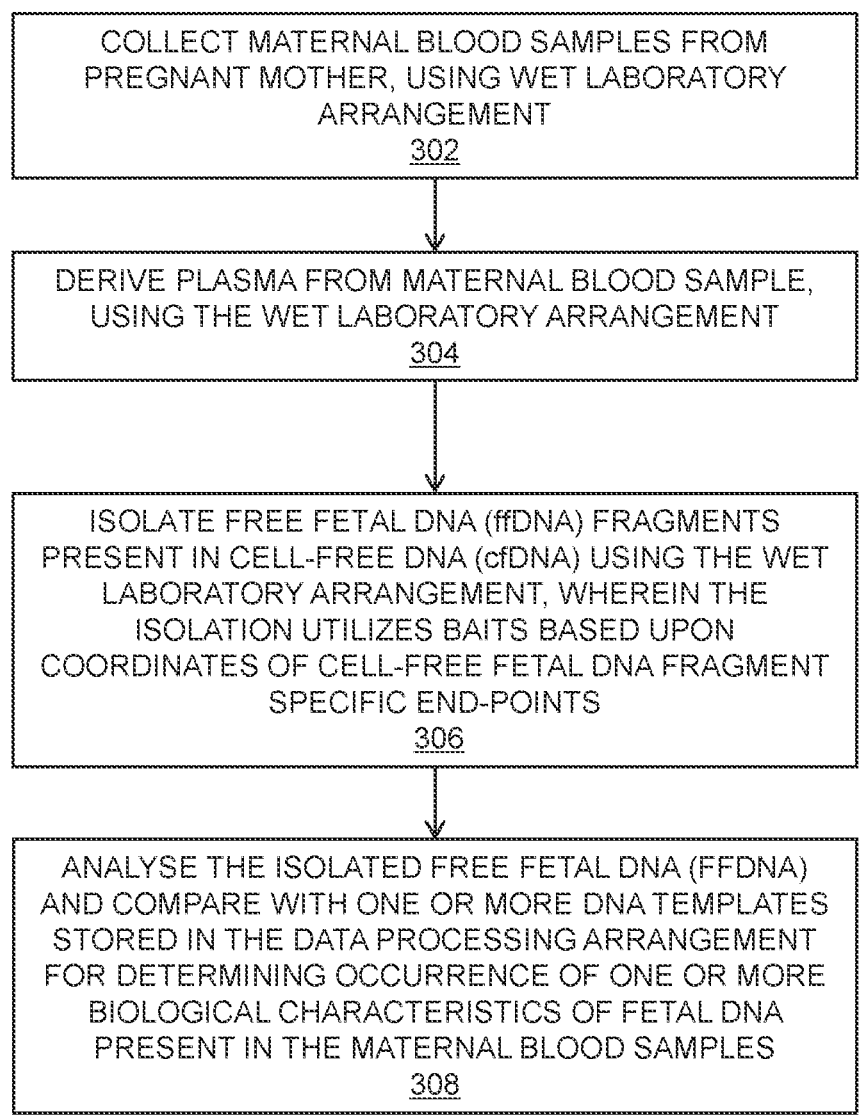
FIG. 3 is an illustration of steps of a method of (for) operating the system of FIGS. 1 and 2 for providing prenatal screening, in accordance with an embodiment of the present disclosure.

In FIG. 3, there is shown a flow chart of a method 300 of (for) using a prenatal screening system (such as prenatal screening system 100 of FIG. 1), in accordance with an embodiment of the present disclosure. At a step 302, the flow chart initiates. At the step 302, a maternal blood sample is collected from a pregnant mother using a wet-laboratory arrangement (such as the wet-laboratory arrangement 102 of FIG. 1). At a step 304, plasma is derived from the maternal blood sample, using the wet-laboratory arrangement. At a step 306, free fetal DNA (ffDNA) fragments present in cell-free DNA (cfDNA) are enriched using the wet laboratory arrangement, wherein the isolation utilizes baits based upon coordinates of cell-free fetal DNA (cffDNA) fragment specific end-points. At a step 308, the isolated free fetal DNA (ffDNA) are analysed and compared with one or more DNA templates stored in the data processing arrangement for determining an occurrence of one or more biological characteristics of fetal DNA present in the maternal blood samples.

In an embodiment, the method 300 of (for) using the prenatal screening system may include using the wet-laboratory arrangement for enriching the cfDNA fragments for providing a plurality of copies of the cfDNA fragments for analysis to the data processing arrangement. Furthermore, the method 300 may include enriching the free fetal DNA fragments by using nucleosome profile to determine the most likely start position and the fetal specific end positions.

In another embodiment, the method 300 of (for) using the prenatal screening system may include using the wet-laboratory arrangement for designing the baits to enrich maternal DNA present in the plasma of the maternal blood sample. Furthermore, the designed baits may be in combination with targeting of genes, wherein the genes are relevant to monogenic clinical disorders.

In yet another embodiment, the method 300 of (for) using the prenatal screening system may include using the wet-laboratory arrangement for isolating and analysing cfDNA fragments in the plasma that start within a nucleosome. Furthermore, the cfDNA fragments correspond to a fetal fraction of the plasma of the maternal blood sample, wherein the cfDNA fragments that start within a nucleosome are relatively shorter in nucleic acid base count than an average length in nucleic acid base count of cfDNA fragments present in the maternal blood sample.

In yet another embodiment, the method 300 of (for) using the prenatal screening system may include using the wet-laboratory arrangement for performing a combined test for prenatal screening of fetal chromosomal abnormalities. In this embodiment, the combined test may include, but is not limited to, a maternal blood test and an ultrasound scan of a fetus.

In yet another embodiment, the method 300 of (for) using the prenatal screening system may include using the data processing arrangement for storing genetic information extracted from the maternal blood samples in a secondary database.

In another embodiment, the method 300 of (for) using the prenatal screening system may include using the data processing arrangement to match the cffDNA fragment in a data base arrangement (such as data base arrangement 106 of FIG. 1) by applying a genetic algorithm (such as the genetic algorithm 212 of FIG. 2).

Although use of the prenatal screening system 100 is described in the foregoing to perform prenatal screening, it will be appreciated that the prenatal screening system may be used to investigate other types of biological problems, and not merely restricted to prenatal screening tasks, for example: cancer risk determination; autistic risk determination; verification of organism performance after performing gene therapy; ionizing radiation damage identification to cell DNA; and/or diabetes risk determination.

Figure 4:
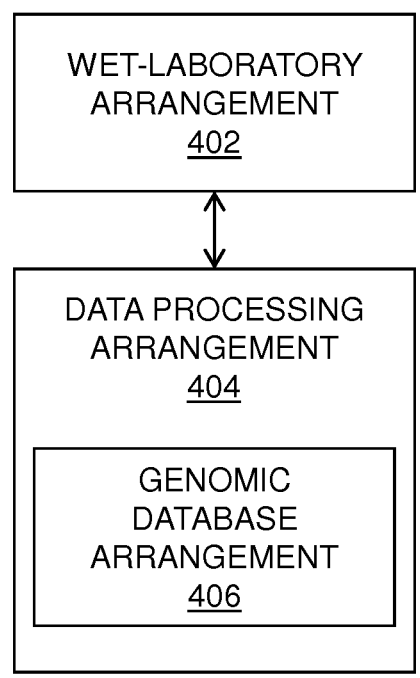
FIG. 4 is a schematic illustration of a screening system, pursuant to the present disclosure.

In overview, embodiments of the present disclosure are also concerned with a screening system as illustrated by 400 in FIG. 4. The screening system 400 includes a wet-laboratory arrangement 402, wherein the wet-laboratory arrangement 402 includes apparatus such as biological sample collection apparatus, centrifuges, PCR rapid gene sequencing apparatus and similar apparatuses. Furthermore, the screening system 400 is operable to process (namely, when in operation, processes) a biological sample in the wet-laboratory arrangement to determine a presence of DNA (namely, cfDNA) fragments therein, and to sequence the DNA fragments.

In operation, the biological sample is obtained from a person, for example a pregnant mother; however, it will be appreciated that paternal blood samples are optionally also employed. For example, using both paternal and maternal blood samples, alternatively tissue samples, is useful when investigating heterozygous alleles, when computing the aforesaid risk score. Optionally, the biological sample is a blood sample or a tissue sample. Optionally, with regard to the pregnant mother, the biological sample is a non-invasive sample, wherein collection of sample does not have an associated risk of miscarriage therewith. However, optionally, the biological sample is supplemented with an invasive sample if required, for example collection of amniotic fluid, collection of placental tissue and so forth. Furthermore, the biological sample includes plasma that includes, as a component part thereof, a mixture of cell-free DNA (cfDNA) fragments. Specifically, the cell-free DNA (cfDNA) may comprise a portion derived from the pregnant mother, from the placenta of the pregnant mother and/or from the fetus. Moreover, the portion of the cell-free DNA (cfDNA) that is derived from the fetus is referred to as being cell-free fetal DNA (cffDNA).

Furthermore, the wet-laboratory arrangement 402 sequences DNA fragments to determine the presence of cell-free DNA (cfDNA). Specifically, DNA fragments present in plasma are amplified and sequenced to generate information representative of sequenced DNA fragments. Optionally, the information representative of sequenced DNA fragments comprises a large amount of nucleic acid-base sequence information. Subsequently, the nucleic acid-base sequence information is processed in the data processing arrangement 404.

In an embodiment, the screening system 400 distinguishes, when in operation, (namely, is operable to distinguish) between cell-free DNA (cfDNA) fragments of maternal origin and cell-free DNA (cfDNA) fragments of placental and/or fetal origin (cffDNA). Specifically, the wet-laboratory arrangement 402 may enrich the cell-free fetal DNA (cffDNA) fragments of placental and/or fetal origin from the cell-free DNA (cfDNA) fragments of maternal origin present in the biological sample. Moreover, data representative of the cell-free DNA (cfDNA) fragments of placental and/or fetal origin are analysed in a data processing arrangement 404.

Moreover, the screening system 400 further includes the data processing arrangement 404, including a genomic database arrangement 406, for receiving information representative of sequenced DNA fragments from the wet-laboratory arrangement 402. Optionally, the data processing arrangement provides feedback data to the wet-laboratory arrangement 402 for controlling various tests performed thereat. Furthermore, the genomic database arrangement 406 stores information comprising genomic mapping data and research data analysing structure, location and sequencing of human genes, and clinical effects of mutations and their co-relation with biological sequences and structures.

Furthermore, the data processing arrangement 404 compares (namely, is operable to compare) information representative of the sequenced DNA fragments against information stored in a genomic database arrangement 406 to provide an assessment score in respect of the biological sample. Optionally, the data processing arrangement 404 may compute results from screening tests implemented upon the biological sample processed by the wet-laboratory arrangement 402. For example, the wet-laboratory arrangement 402 may provide a prenatal screening service, but is not limited thereto. More optionally, the data processing arrangement 404 may compare data provided by sequencing of DNA fragments against information stored in the genomic database arrangement 406 to assess a risk of a genetic disorder in the compared DNA fragments. Specifically, cell free-DNA fragments are compared against information stored in the genomic database arrangement 406. In an exemplary embodiment, the information representative of the sequenced DNA fragments may comprise a sequential arrangement of 'A-T-G-C-A-T-G-C' DNA base pairs with an anomaly 'A-G-T-C'. In such an embodiment, the data processing arrangement 402 may compare the anomaly against sequential arrangements of DNA stored in the genomic database 406. Subsequently in the embodiment, the data processing arrangement 404 may assess if the anomaly may or may not cause a genetic disorder. Additionally, the data processing arrangement 404 may compare and provide the assessment score representative of a risk to the fetus of inheriting or acquiring a genetic disorder. It will be appreciated that the DNA base pairs A, T, G, C (adenine, thymine, guanine and cytosine) are for illustrative purposes only and do not represent the actual arrangement of the DNA base pairs which may be responsible for a specific disease.

It will be appreciated that there are one or more stochastic ratings, associated with the information representative of the sequenced DNA fragments provided by the wet-laboratory arrangement 402. Specifically, the one or more stochastic ratings are representative of measurements of stochastic noise during prenatal screening. More specifically, the stochastic noise may increase a risk of a false assessment score (such as, a false negative score or a false positive score) when computed by the data processing arrangement 404. Moreover, the risk of a false assessment score contributes towards stochastic and/or systemic uncertainty present in the assessment score. Additionally, a higher stochastic and/or systemic uncertainty reduces confidence in results provided by the screening tests.

The screening system 400 applies in operation (namely, is operable to apply) a modification to one or more stochastic ratings associated with the information representative of the sequenced DNA fragments. Specifically, the modification is applied to one or more stochastic ratings to reduce a stochastic and/or systemic uncertainty present in the assessment score. More specifically, the modification is applied to one or more stochastic ratings using secondary information provided to the screening system 400.

In an embodiment, the secondary information provided to the screening may refer to genetic information, environmental conditions, nutritional information related with diet and so forth associated with the person providing the biological sample. Specifically, the secondary information relates to factors that may affect a risk of inheriting a congenital defect, for example lifestyle parameters (for example, alcohol intake, tobacco smoking), medical history of operations, environmental radiation exposure parameters, cosmic ray exposures, and so forth.

In an embodiment, the screening system employs in operation (namely, is operable to employ) at least one of following scores when computing the modification in the data processing arrangement:
 (a) a genome locality score, wherein the genome locality score includes a likelihood of mutation within a region;
 (b) a sequence error score, wherein the sequence error score includes a likelihood of a given nucleic acid base is a result of PCR infidelity during template amplification and/or a miscall during a sequencing process;
 (c) a patient modifier score, wherein the patient modifier score includes details from external sources; and
 (d) a mosaicism detection score, wherein the mosaicism detection score includes a likelihood of variants occurring in a region of imbalanced maternal genotype In an embodiment, the genome locality score is calculated to include a frequency of identification (namely, calling) of an incorrect genotype. Specifically, the genotype may be in a given area of a genome or chromosome. More specifically, the incorrect genotype may be identified due to issues of the genomic architecture. Examples of issues of the genomic architecture include, but are limited to, one or more occurrences of repetitive sequence, low genetic conservations, gene sequence topologies. Furthermore, genome locality score relates to likelihood of mutation within a region. Specifically, the region may be a region of interest. In an example, the region of interest may be assay capture areas that may extend to all exomes or a whole given genome. Moreover, the data processing arrangement 404 may calculate the genome locality score.

In an embodiment, the likelihood of mutation within the region is calculated on a basis of frequencies of change susceptible to occur to the region and/or frequencies of calling spurious variants in the region. Specifically, the genome locality score takes into estimation, a likelihood of one or more changes to occur in a region. Moreover, frequencies of calling spurious variants in the region are taken into estimation. In an embodiment, the screening system 400 converts (namely, is operable to convert) the genome locality score into a weight for a particular locus. Specifically, the weight of the genome locality score is representative of an indication of a potential stochastic error in the genome locality score.

In an embodiment, the sequence error score includes a likelihood of an error during amplification and/or sequencing of DNA fragments. Specifically, the DNA fragments are amplified and sequenced to generate information representative of sequenced DNA fragments. Consequently, polymerase chain reactions (PCR) may be implemented during such amplification and sequencing. Specifically, polymerase chain reactions (PCR) employ a DNA polymerase for accurate replication of DNA fragments. Subsequently, an error in amplification and sequencing (namely, replication) by the DNA polymerase is referred to PCR infidelity. Therefore, the sequence error includes likelihood that a given nucleic acid base is generated due to PCR infidelity during amplification of the template (namely, DNA fragments). Furthermore, an error in the sequencing process is referred as being a miscall during sequencing process. Specifically, the sequencing process includes different nucleic acid base concentrations that may lead to the miscall.

In an embodiment, unique molecular indices may be added, for example as a quality tracer, to the biological sample for identifying unique and original DNA fragments, which may otherwise have been misinterpreted due to errors introduced during amplification. Therefore, the potential stochastic error in the genome locality score is susceptible to being decreased by employing the quality tracer. Optionally, aforementioned one or more barcodes are employed as a quality tracer through amplification and PCR, because the barcodes can be known a priori to performing such amplification and PCR. In other words, the barcodes not only allow for more reliable DNA fragment readout, but also allow an intrinsic error rate of amplification and PCR processes to be quantified by measurement, for example for use in modifying a computation of the final risk score.

In an embodiment, the sequence error score is calculated using a maternal genetic sequence. Specifically, the DNA fragments employed for amplification and sequencing may be of maternal origin. Furthermore, estimation of sequence error score is relatively less complex using information obtained from the maternal genetic sequence. In an embodiment, the screening system 400 applies (namely, is operable to apply) the sequence error score as a weight and to modify a confidence in a base call. Specifically, the weight of the sequence error score is a representative of accuracy of the amplification and sequencing process.

In an embodiment, the patient modifier score is employed when computing the modification in the data processing arrangement 404. Specifically, the patient modifier score includes variations in a phenotype influenced by factors such as diet, climate, exposure to chemicals or ionizing radiation, illness and so forth, for example as aforementioned. Optionally, the information for external sources includes at least information received from abnormality scans. Specifically, the abnormality scan may be performed during pregnancy to ensure a healthy development of the fetus. More specifically, any anomaly and/or abnormality is reported to include in the patient modifier score by the screening system 400.

In an embodiment, the patient modifier score may include expectations of de novo mutations in line with paternal age. For example, more de novo mutations may be expected in foetuses with older fathers and thus, may contribute towards a higher patient modifier score. Optionally, the patient modifier score may include dominant-recessive inheritance. For example, a risk of a child inheriting diabetes having parents with recessive gene responsible for diabetes may be more. In an embodiment, the screening system 400 converts in operation (namely, is operable to convert) details from the external sources into a weight.

In an embodiment, the mosaicism detection score includes a likelihood of variant occurring in a region of imbalanced maternal genotype. Specifically, the cell-free DNA (cfDNA) fragments of the placental origin may potentially display genetic abnormalities, even when such abnormalities may not exist in the fetus. Therefore, maternal genotypes may provide an indication if there is a real risk of abnormality in the fetus or if it is a false call. In another embodiment, the false call may be due to an imbalance in maternal allele frequencies. Beneficially, for comparison, a maternal blood sample prior to pregnancy is obtained and sequenced using amplification and PCR, as a reference against which the cfDNA fragments obtained during pregnancy are compared. By such an approach, alleles associated with a fetus, or at least with a placenta of the fetus, are more readily distinguished from maternal alleles. When a paternal blood sample is available, identifying fetal or placental DNA fragments from a maternal blood sample can be determined with even greater certainty, thereby improving an accuracy of the aforementioned risk score, when computed.

In an embodiment, the screening system 400 combines in operation (namely, is operable to combine) the genome locality score, the sequence error score, the patient modifier score and/or mosaicism detection score to modify the confidence of a call. Specifically, the scores take into account the factors that may cause an error in the assessment score. Therefore, when such factors are accounted for in the assessment score, the confidence of a call generated thereby may be positively affected.

In an embodiment, the biological sample containing cfDNA fragments therein is extracted from a pregnant woman in a non-invasive manner. Specifically, the biological sample extracted from the pregnant woman may be extracted in a non-invasive manner to prevent, or reduce, a risk of miscarriage. Furthermore, examples of non-invasive manners may include techniques which may not involve extraction of sample from the amniotic sac.

Figure 5:
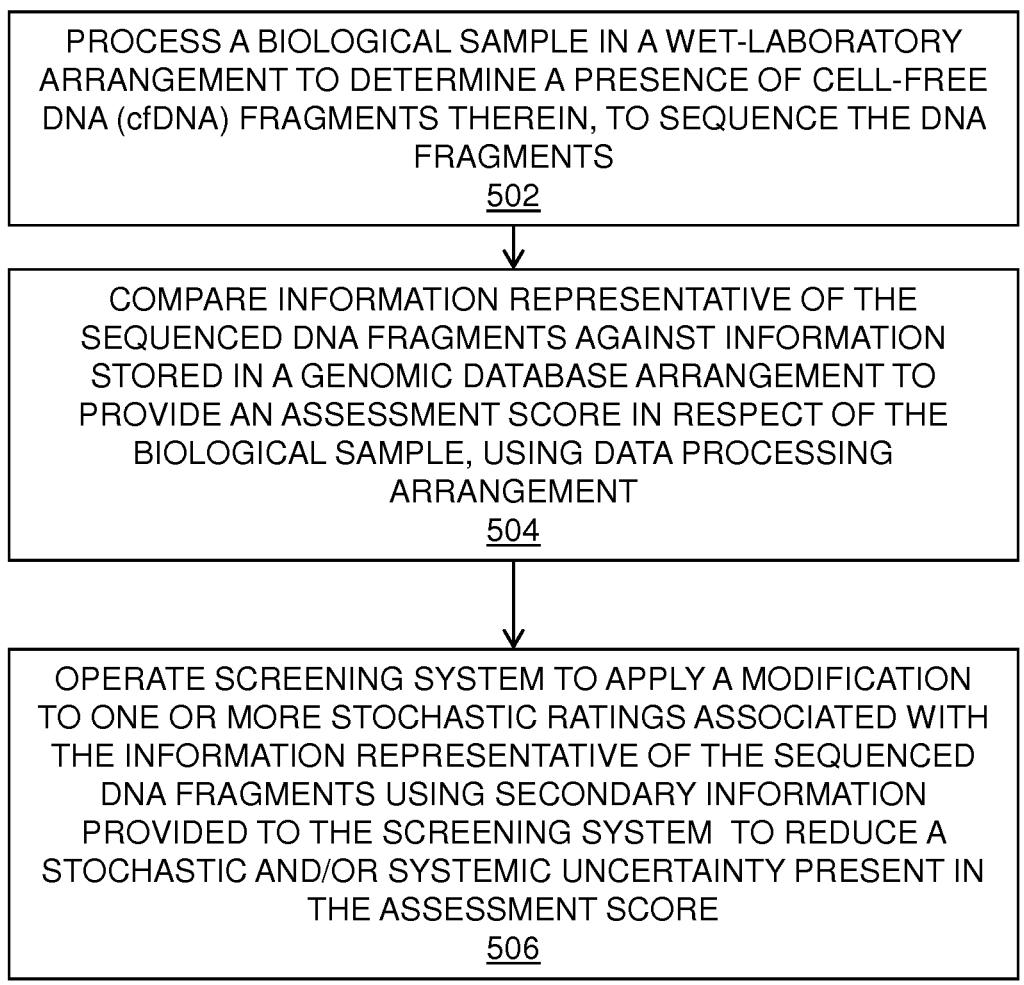
FIG. 5 is an illustration of steps of a method of (for) using the screening system of FIG. 5, pursuant to the present disclosure.

In FIG. 5, there is shown a flow chart of a method 500 of (for) using a screening system (such as the screening system 400 of FIG. 4) pursuant to the present disclosure. At a step 502, the flow chart initiates. At the step 502, a biological sample is processed in a wet-laboratory arrangement to determine a presence of cell-free DNA (cfDNA) fragments therein, to sequence the DNA fragments. At a step 504, information representative of the sequenced DNA fragments is compared against information stored in a genomic database arrangement, using a data processing arrangement to provide an assessment score in respect of the biological sample. At a step 506, the screening system is operated to apply a modification to one or more stochastic ratings associated with the information representative of the sequenced DNA fragments using secondary information provided to the screening system to reduce a stochastic and/or systemic uncertainty present in the assessment score.

The steps 502 to 506 are only illustrative and other alternatives can also be provided where one or more steps are added, one or more steps are removed, or one or more steps are provided in a different sequence without departing from the scope of the claims herein. In an embodiment, the method 500 includes distinguishing between cell-free DNA fragments of maternal original from cell-free DNA fragments of placental and/or fetal origin.

In another embodiment, the method 500 includes employing at least one of following scores when computing the modification in the data processing arrangement:
  (a) a genome locality score, wherein the genome locality score includes a likelihood of mutation within a region;
  (b) a sequence error score, wherein the sequence error score includes a likelihood of a given nucleic acid base is a result of PCR infidelity during template amplification and/or a miscall during the sequencing process;
  (c) a patient modifier score, wherein the patient modifier score includes details from external sources; and
  (d) a mosaicism detection score, wherein the mosaicism detection score includes a likelihood of variants occurring in a region of imbalanced maternal genotype.

In yet another embodiment, the method 500 includes calculating the likelihood of a mutation within the region on the basis of frequencies of change is to occur to the region and/or frequencies of calling spurious variants in the region. In an embodiment, the method 500 includes calculating the sequence error score using maternal genetic sequence.

In an embodiment, the method 500 includes receiving information from abnormality scans. In another embodiment, the method 500 includes converting the genome locality score into a weight for a particular locus. Optionally, the method 500 includes applying the sequence error score as a weight and to modify confidence in a base call. More optionally, the method 500 includes converting the details from external sources in to a weight.

Optionally, the method 500 includes combining the genome locality score, the sequence error score, the patient modifier score and/or mosaicism detection score to modify the confidence of a given call. Optionally, the method 500 includes extracting the biological sample containing cfDNA fragments therein from a pregnant woman in a non-invasive manner.

Optionally, the aforementioned method 500 of (for) using the screening system is implemented by using a computer program product comprising a non-transitory computer-readable storage medium having computer-readable instructions stored thereon, the computer-readable instructions being executable by a computerized device comprising processing hardware.

In overview, the aforementioned known approaches, when performing an analysis of a maternal blood sample for testing or diagnostic purposes, do not include a multitude of information relevant in determining risk of a given child having a disease. Specifically, the multitude of information includes, but is not limited to, patient data, data regarding the exact genes being screened, sequence run information.

The NGPS knowledgebase, employed in the present disclosure, may function as a repository for information pertaining to one or more targeted assay approaches that may be employed for implementation of NGPS. The 'NGPS knowledgebase' optionally may include a database to store information regarding a given patient. Specifically, the information may include data relating to one or more regions of the human genome included in an assay, indication of sequencing error rate of a given run, and algorithms to allow the 'NGPS knowledgebase' to be updated and associated models to be re-evaluated. Beneficially, the 'NGPS knowledgebase' may inform, and be informed by, NGPS analyses that are performed in conjunction therewith. Specifically, such information exchange may allow improvement and evolution of 'NGPS knowledgebase'.

The aforementioned 'NGPS knowledgebase' may be composed of a plurality of parts. A first part P1, considered to be foremost, concerns construction of a database arrangement, for example including one or more databases, containing information directly relevant to a screening process being performed for the given person, for example for a pregnant mother. Other parts of the 'NGPS knowledgebase' include:
  (a) a second part P2 concerning a genomic capture area database;
  (b) a third part P3 concerning a patient information database; and
  (c) a fourth part P4 concerning a sequencing run database.

Furthermore, the parts P1 to P4 may store information; the 'NGPS knowledgebase' may include one or more algorithms that may be built to extract information, to populate the aforementioned one or more databases, and to convert the information into computationally useable weighting or confidence parameters. In addition, the 'NGPS knowledgebase' may include one or more algorithms that are operable to update and remodel existing data set information with every new data set of additional information. Therefore, the 'NGPS knowledgebase' may be operable to employ artificial intelligence (AI) to learn from these databases. For example, an artificial intelligence (AI) engine may include a hierarchical layered configuration of computer-implemented neural networks that are operable to provide pseudo-analogue variable state machines for decision making purposes; the neural networks are optionally trained using synthesized data before being exposed to real data derived from processing biological samples, such that the real data iteratively improves discernment provided in operation by the neural networks.

Furthermore, the components of the 'NGPS knowledgebase' may include genomic capture area database; sequencing information database; and patient information database.

The genomic capture area database may contain information relating to a capture area of an NGPS assay employed when implementing embodiments of the present disclosure. Furthermore, the genomic capture area database is concerned with only the regions, of the genome, that are on target for the screening assay. The genomic capture area database may include information indicative of:
  (i) a likelihood of erroneous calling in these regions of the genome; and
  (ii) a likelihood of mutation at the genetic level as well as the known deleterious variants and their associated phenotype (HPO terms).

The sequencing information database may contain information about each sample including library preparation quality scores, a degree to which sequencing errors have been observed within the sequence data for sequencing run executed for each sample, an estimated fetal fraction for each sample, and an estimated percentage coverage of the genome by cell-free DNA for each sample. Such a store of information enables both an investigation of patterns in sequencing results obtained, that may not be related to associated underlying genetics, and the potential to learn from challenges due to sequencing technology limitations or artefacts.

Generally, performing analyses in an absence of valuable collected phenotypic data on patient phenotype leads to a sub-optimal performance of analyses as all regions of the genome may be considered with equal weight, even though this may not be logically sound reasoning; in contradistinction, embodiments of the present disclosure utilize phenotypic data on patient phenotype. In an exemplary embodiment, in an event of information regarding an abnormal scan results, the event may lend evidence to sequencing information that may be present, but not in sufficient depth to be highlighted. Furthermore, by utilizing pieces of information in combination, there may be provided an improvement in sensitivity and detective power when performing prenatal screening, beneficially leading to a reduction in the rate of false negatives. Moreover, the patent information database may help to reduce the rate of false positives, such as including the age of the father in an analyses as this is known to have an impact on the mutational rate in the germ line and thus the number of 'de novo' mutations that are expected to be encountered.

Embodiments of the present disclosure may include an algorithm to update and restructure information in the aforementioned one or more databases of the NGPS system, for example in a recursive or iterative manner.

Thus, in embodiments of the present disclosure, computing new error scores and re-evaluating computational assumptions in light of new data supplied to the one or more aforementioned databases is an important essential of the 'NGPS knowledgebase'.

In another aspect, embodiments of the present disclosure provide a prenatal screening system, wherein the prenatal screening system includes a wet-laboratory arrangement that processes a blood sample to determine cell-free DNA readout data from the blood sample, and a data processing arrangement that processes the cell-free DNA readout data with reference to information stored in a database arrangement to generate a risk score indicative of whether or not there are genetic abnormalities in the blood sample that are indicative of fetal abnormalities, characterized in that the prenatal screening system uses (namely, is operable to use) secondary data describing a donor of the blood sample to modify data processing performed in the data processing arrangement when processing selective regions of the cell-free DNA readout data when generating the risk score.

In yet another aspect, embodiments of the present disclosure provide a method of (for) using a prenatal screening system, wherein the prenatal screening system includes a wet-laboratory arrangement that processes a blood sample to determine cell-free DNA readout data from the blood sample, and a data processing arrangement that processes the cell-free DNA readout data with reference to information stored in a database arrangement to generate a risk score indicative of whether or not there are genetic abnormalities in the blood sample that are indicative of fetal abnormalities, characterized in that the method includes operating the prenatal screening system to use secondary data describing a donor of the blood sample for modifying data processing performed in the data processing arrangement for processing selective regions of the cell-free DNA readout data when generating the risk score.

Figure 6:
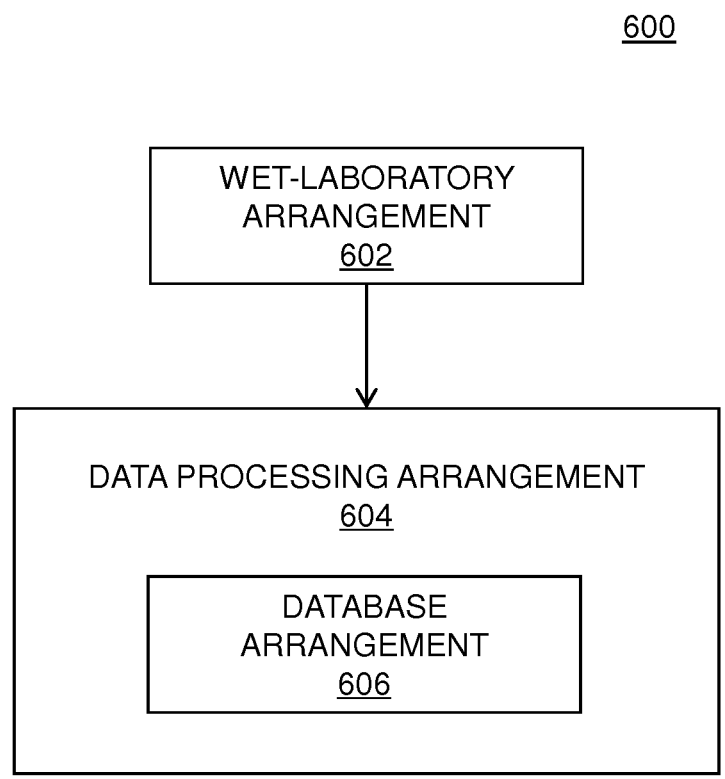
FIG. 6 is a schematic illustration of a next generation prenatal screening system, in accordance with an embodiment of the present disclosure (FIG. 1)

In FIG. 6, there is shown an illustration of a prenatal screening system 600, in accordance with an embodiment of the present disclosure. The prenatal screening system 600 includes a wet-laboratory arrangement 602 and a data processing arrangement 604. The data processing arrangement 604 further includes a database arrangement 606. The wet-laboratory arrangement 602 of the prenatal screening system 600 is operable to exchange instructions and data with the data processing arrangement 604.

Generally, the wet-laboratory arrangement 602 of the prenatal screening system 600 processes in operation (namely, is operable to process) a maternal blood sample to determine cell free DNA data from the blood sample. Furthermore, the data processing arrangement 604 of the prenatal screening system 600 processes (namely, is operable to process) the cell free DNA readout data with reference to information stored in the database arrangement 606 to generate, namely compute, a risk score. The risk score generated with reference to information stored in the database arrangement 606 is indicative of whether or not there are genetic abnormalities in the blood sample that are indicative of fetal abnormalities. Moreover, the prenatal screening system 600 uses in operation (namely, is operable to use) secondary data describing a donor of the blood sample for modifying data processing performed in the data processing arrangement 604 for processing selective regions of the cell-free DNA readout data while generating the risk score.

In an embodiment, the wet-laboratory arrangement 602 may include apparatuses for taking maternal blood samples, ultrasound scanning apparatus for fetal imaging, PCR sequencing apparatus, centrifuges, gel electrophoresis DNA sequencing apparatus, microscopes and so forth. For example, the wet-laboratory arrangement 602 may include apparatus manufactured by Illumina® Inc. that perform gene sequencing tasks. The data processing arrangement 604 includes a database arrangement 606 including a plurality of databases, as aforementioned. The data processing arrangement 604 also includes data communication connections to networks such as the Internet®, for example for accessing various external databases associated with university research departments and hospitals. For example, the external databases may include but not limited to Gen-Bank®, dbEST®, dbSTS®, EMBL® (European Molecular Biology Laboratory) and DDBJ® (DNA Databank of Japan). BLAST® or similar tools can be used to search the identified sequences against a sequence database.

In an embodiment, the blood sample processed in the wet-laboratory arrangement 602 may be a maternal blood sample. In this embodiment, the cell-free DNA readout data may be determined from fragments of DNA present in a plasma fraction of the maternal blood sample. Furthermore, in this embodiment, the wet-laboratory arrangement 604 amplifies in operation (namely, is operable to amplify) the fragments of DNA to provide amplified DNA for nucleic acid base sequencing or readout to generate the cell-free DNA readout data. In this exemplary embodiment, the wet-laboratory arrangement 602 may include a PCR or RT-PCR to amplify the free fetal DNA fragments to provide a plurality of copies of the free fetal DNA to the data processing arrangement 604 when accessing genetic information in the database arrangement 606.

According to an embodiment, the selective regions may be determined by accessing one or more databases of the database arrangement 606. In this embodiment, the database arrangement 606 may include, but not limited to, Gen-Bank®, dbEST®, dbSTS®, EMBL® (European Molecular Biology Laboratory) and DDBJ® (DNA Databank of Japan). BLAST® or similar tools that can be used to search the identified sequences against a sequence database. Furthermore, in this embodiment, the prenatal screening system 600 updates in operation (namely, is operable to update) the one or more databases of the prenatal screening system recursively or iteratively depending upon a determined accuracy of the risk score to one or more subsequent fetal investigations.

In yet another embodiment, the secondary data may be determined by non-invasive procedures. In such embodiment, the subsequent fetal investigation involves executing one or more invasive sampling of tissue or liquids in respect of the fetus. In this embodiment, non-invasive procedures may include, but not limited to, maternal blood test and/or ultrasonic scan of a fetus.

In another embodiment, the one or more database may be implemented as a NGPS knowledgebase. Furthermore, analyses of the NGPS knowledgebase may be recalibrated to include and incorporate information that is specific to a donor of the blood sample. In this embodiment, the NGPS knowledgebase may include phenotypic information that may be employed in data analyses performed by the data processing arrangement 600 while generating the risk score.

In an exemplary embodiment, the data processing arrangement 606 may concentrate, namely employs its computational resources, on testing certain selective portions of a given DNA depending upon secondary indications, such as abnormalities in parental DNA, abnormalities identified in ultrasound scans, and so forth. Moreover, the data processing arrangement 604 is operable to update and evolve recursively information included in the one or more databases depending upon test results obtained from using the prenatal screening system 600 on maternal blood samples, and from information, for example tests undertaken by third parties, obtained from external databases.

Beneficially, the prenatal screening system 600 may employ one or more the aforementioned parts P1 to P4. Optionally, the prenatal screening system 600 may not be limited to use the parts P1 to P4, and may access other external databases.

In another exemplary embodiment, the prenatal screening system 600 may optionally employ an artificial intelligence (AI) engine implemented using an array of RISC processors (for example, an array of proprietary ARM Cortex® processors) with associated data memory for implementing many hundred million pseudo-analogue variable state machines arranged in a hierarchical manner for providing data processing and data analysis within the data processing arrangement 606; thereby, machine deduction processes can be implemented, for example based upon use of "black box" neural network analogue variable state machines. Optionally, synthetically generated data is used to train the algorithm, before it is exposed to real DNA data derived from biological samples, as aforementioned.

Figure 7:
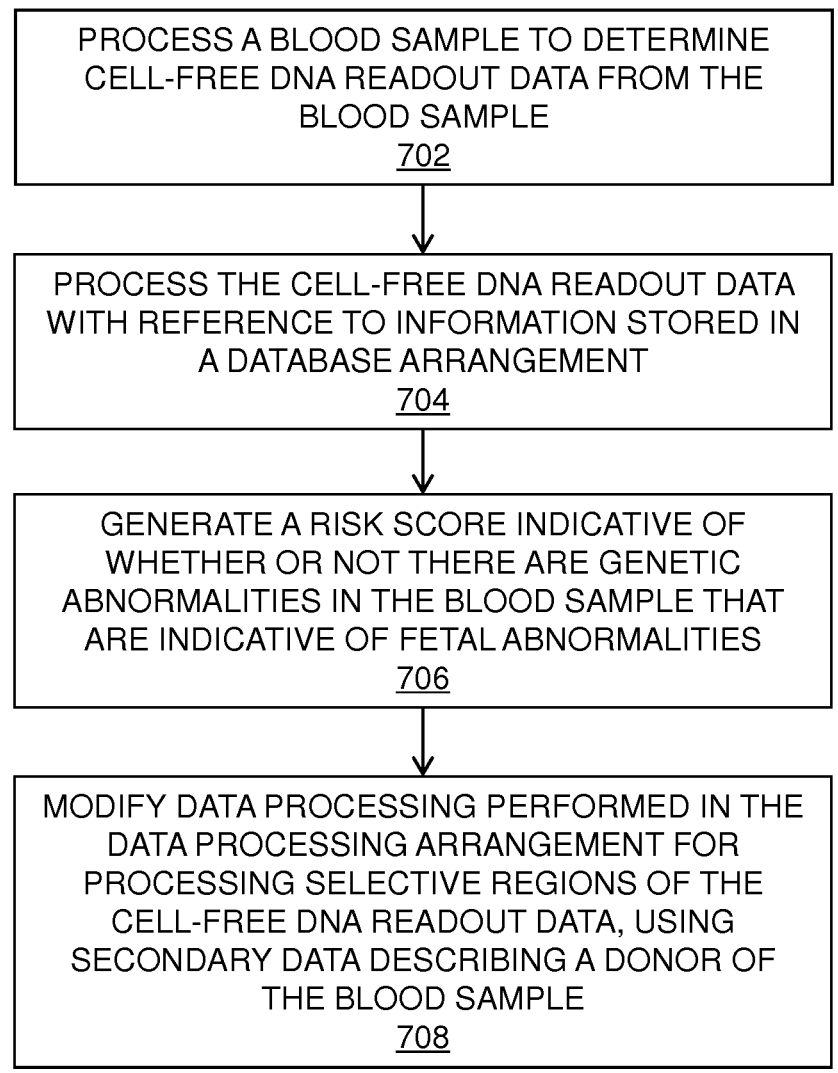
FIG. 7 is an illustration of steps of a method of (for) operating the system of FIG. 6 for providing next generation prenatal screening pursuant to the present disclosure.

In FIG. 7, there is shown a flow chart of method 700 of (for) using a prenatal screening system (such as prenatal screening system 700 of FIG. 6), in accordance with an embodiment of the present disclosure. At a step 702, the flow chart initiates. At the step 702, a blood sample is processed to determine cell-free DNA readout data from the blood sample. At a step 704, the cell-free DNA readout data is processed with reference to information stored in a database arrangement. At a step 706, a risk score indicative of whether or not there are genetic abnormalities in the blood sample that are indicative of fetal abnormalities is generated. At a step 708, data processing performed in the data processing arrangement for processing selective regions of the cell-free DNA readout data is processed using secondary data describing a donor of the blood sample.

In an embodiment, the blood sample processed in the wet-laboratory arrangement may be a maternal blood sample. In this embodiment, the cell-free DNA readout data may be determined from fragments of DNA present in a plasma fraction of the maternal blood sample. Further in this embodiment, the method 700 may include using wet-laboratory arrangement to amplify the fragments of DNA to provide amplified DNA for nucleic acid base sequencing or readout to generate the cell-free DNA readout data. In this exemplary embodiment, the method 700 may include using a PCR or RT-PCR for amplifying the free fetal DNA fragments for providing a plurality of copies of the free fetal DNA to the data processing arrangement for accessing genetic information in the database arrangement.

In another embodiment, the method 700 may include determining the selective regions by accessing one or more databases of the database arrangement, wherein the prenatal screening system may be operable to update the one or more databases recursively or iteratively depending upon a determined accuracy of the risk score to one or more subsequent fetal investigations. In this embodiment, the method 700 may include determining the secondary data by non-invasive procedures, and determining the subsequent fetal investigation by executing one or more invasive sampling of tissue or liquids in respect of the fetus. In this embodiment, by non-invasive procedures may include but not limited to maternal blood test and/or ultrasonic scan of a fetus.

In yet another embodiment, the method 700 may include implementing the one or more databases as a NGPS knowledgebase, wherein the NGPS knowledgebase includes analyses that are recalibrated in operation to include and incorporate information that is specific to a donor of the blood sample. In this embodiment, the method 700 may include arranging the NGPS knowledgebase to include phenotypic information that may be employed in analyses of data performed by the data processing arrangement when generating the risk score.

Beneficially, the method 700 may include using the prenatal screening system to employ one or more the aforementioned parts P1 to P4, for example a plurality of the parts P1 to P4. Optionally, the prenatal screening system may not be limited to use these parts P1 to P4, and can access other external databases.

Optionally, the aforementioned method 700 of using the prenatal screening system is implemented by using a computer program product comprising a non-transitory computer-readable storage medium having computer-readable instructions stored thereon, the computer-readable instructions being executable by a computerized device comprising processing hardware.

Figure 8:
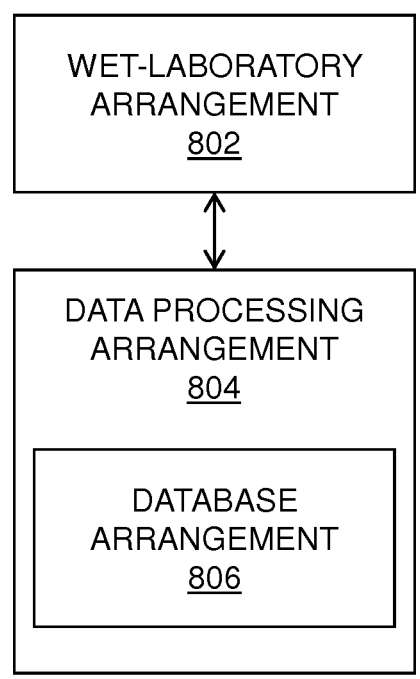
FIG. 8 is a block diagram of a prenatal screening system, in accordance with an embodiment of the present disclosure.

Referring to FIG. 8, there is shown a block diagram of a prenatal screening system 800, in accordance with an embodiment of the present disclosure. The prenatal screening system 800 includes a wet-laboratory arrangement 802, wherein the wet-laboratory arrangement 802 includes apparatus such as blood sample collection apparatus, centrifuges, PCR rapid gene sequencing apparatus and similar apparatuses. For example, the wet-laboratory arrangement 802 includes apparatus manufactured by Illumina® Inc. for performing gene sequencing tasks. Furthermore, the prenatal screening system 800 is operable to process a blood sample in the wet-laboratory arrangement 802 to obtain cell-free DNA readout data therefrom.

In an embodiment, the prenatal screening system 800 performs in operation (namely, is operable to perform) non-invasive molecular diagnosis of a fetus which, on ultrasound testing (for example, ultrasound scanning), presents with for example, a skeletal abnormality and/or a cardiac abnormality. Optionally, the wet-laboratory arrangement 802 performs in operation (namely, is operable to perform) non-invasive molecular diagnosis of a fetus, such as ultrasound testing information, to detect fetal abnormalities, such as a skeletal abnormality and/or a cardiac abnormality. Furthermore, the prenatal screening system 800, optionally, the wet-laboratory arrangement 802 generates in operation (namely, is operable to generate) an ultrasonic image or video of the fetus, to deduce the possibility of a fetal abnormality identified from the ultrasonic test.

Optionally, the wet-laboratory arrangement 802 performs in operation (namely, is operable to perform) a combined test for prenatal screening of fetal genetic abnormalities. More optionally, the combined test may include, but is not limited to, a maternal blood test and an ultrasound scan of a fetus. Furthermore, the wet-laboratory arrangement 802 provides in operation (namely, is operable to provide) information representative of the combined test of the fetus.

In operation, the tissue sample, for example a blood sample, is obtained from a person, for example a pregnant mother. Optionally, with regard to the pregnant mother, the blood sample is a non-invasive sample, wherein collection of sample does not have an associated risk of miscarriage therewith. Furthermore, the blood sample includes plasma that includes, as a component part thereof, a mixture of cell-free DNA (cfDNA). Specifically, the cell-free DNA (cfDNA) may comprise a portion derived from the pregnant mother, from the placenta of the pregnant mother and/or from a fetus of the pregnant mother.

In an embodiment, a genetic abnormality may include genetic diseases that are present in the DNA sequences of a given mother. Specifically, such genetic diseases may or may not be inherited by a fetus of the given mother. Additionally, a fetal abnormality may include diseases that may be inherited or that may arise de novo in the fetus.

Moreover, the prenatal screening system 800 further includes a data processing arrangement 804, including a database arrangement 806, for receiving cell-free DNA readout data from the wet-laboratory arrangement 802. Optionally, the data processing arrangement 804 provides feedback data to the wet-laboratory arrangement 802 for controlling various tests performed thereat. Furthermore, the database arrangement 806 stores information comprising genomic mapping data and research data analysing structure, location and sequencing of human genes, and clinical effects of mutations and their co-relation with biological sequences and structures. Furthermore, the wet-laboratory arrangement 802 may amplifies in operation (namely, is operable to amplify) the fragments of DNA to provide amplified DNA for nucleic acid base sequencing or readout to generate the cell-free DNA readout data. In this exemplary embodiment, the wet-laboratory arrangement 802 may include a PCR for amplifying the free fetal DNA fragments for providing a plurality of copies of the free fetal DNA to the data processing arrangement 804 for accessing genetic information in the database arrangement 806. Additionally, the data processing arrangement 804 also includes data communication connections to networks such as the Internet®, for example for accessing various external databases associated with university research departments and hospitals.

Furthermore, the data processing arrangement 804 processes in operation (namely, is operable to process) the cell-free DNA readout data with reference to information stored in a database arrangement 806 to generate a risk score indicative of whether or not there are genetic abnormalities in the blood sample that are indicative, for example, of fetal abnormalities. Specifically, a risk score may be associated with a given fetus, wherein a higher risk score is indicative a higher possibility of a fetal abnormality. Furthermore, the risk score is generated after processing of cell-free DNA readout data with reference to information stored in the database arrangement 806. Specifically, the cell-free DNA readout data may correspond to a given genomic information in the database arrangement 806. Furthermore, such genomic information may be linked with a risk of a given genetic abnormality, as aforementioned. In an exemplary embodiment, the cell-free DNA readout data may comprise a sequential arrangement of 'A-T-G-C-A-T-G-C' DNA base pairs with an anomaly 'A-T-G-C'. In such an embodiment, the data processing arrangement 802 may compare the anomaly against sequential arrangements of DNA stored in the database arrangement 806. Subsequently in the embodiment, the data processing arrangement 804 may assess if the anomaly may or may not cause a genetic disorder. Additionally, the data processing arrangement 804 may compare and provide the risk score representative of a risk to the fetus of inheriting or acquiring the genetic disorder. It will be appreciated that the DNA base pairs A, T, G, C represent DNA base pairs adenine, thymine, guanine and cytosine for illustrative purposes only and do not represent the actual arrangement of the DNA base pairs which may be responsible for a specific disease.

In an embodiment, fragments of cell-free DNA are generated in the prenatal screening system 800 by employing enzymic digestion. Specifically, cell-free DNA may undergo natural enzymic digestion. More specifically, strands of DNA may be fragmented (namely, cleaved) using enzymes.

Furthermore, action sites of enzymes on the cell-free DNA may not be experimentally controlled.

Figure 9:
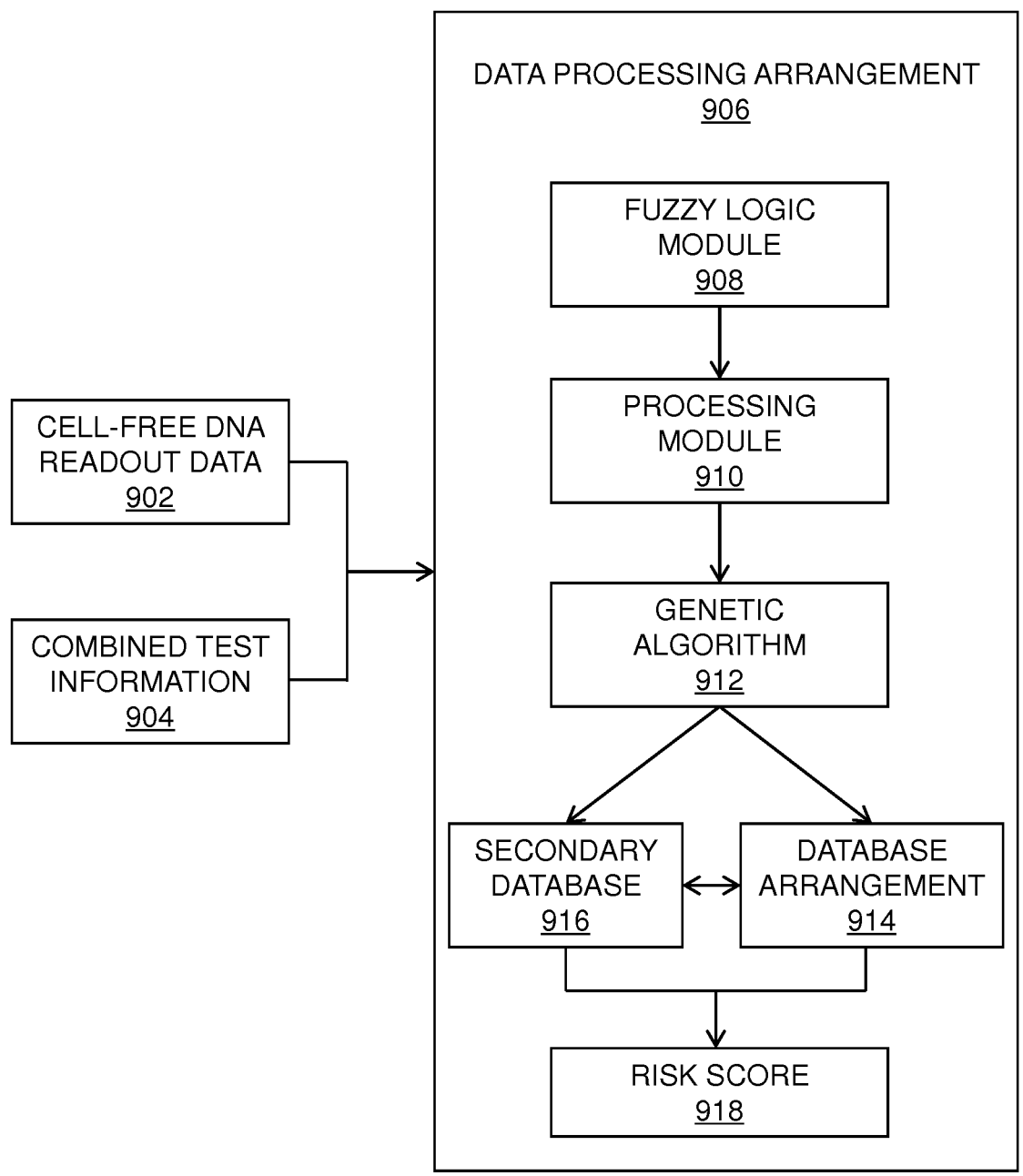
FIG. 9 is an illustration of a Kalman filter equivalent representation of the prenatal screening system of FIG. 8, in accordance with an embodiment of the present disclosure.

Referring to FIG. 9, there is shown an illustration of a Kalman filter equivalent representation 900 of the prenatal screening system (such as the prenatal screening system 800 of FIG. 8), in accordance with an embodiment of the present disclosure. The Kalman filter equivalent representation 900 includes the cell-free DNA readout data 902 and the information representative of combined test of the fetus 904 to a data processing arrangement 906 (such as data processing arrangement 804 of FIG. 8). The data processing arrangement 906 implements in operation a Kalman filter on the cell-free DNA readout data 902 information representative of combined test of the fetus 904. The data processing arrangement 906 further includes a fuzzy logic module 908, a processing module 910, a genetic algorithm 912 for processing the cell-free DNA readout data with reference to the information stored in a database arrangement 914 (such as the database arrangement 806 of FIG. 8), a secondary database 916 (such as secondary database for storing the risk score 918 received from the processing module 910. In this embodiment, the data processing system 906 implements in operation (namely, is operable to implement) the Kalman filter on the genetic information received after prenatal screening tests performed by the wet-laboratory arrangement 802. Furthermore, the genetic algorithm 912 generates (namely is used to compute) in operation the risk score by processing the cell-free DNA readout data with reference to the information stored in a database arrangement 914.

In an exemplary embodiment, a plasma sample derived from the aforementioned blood sample includes DNA sequences that are enriched using hybridization. Specifically, the hybridization enrichment is performed using baits targeted at genes that are susceptible to causing fetal illnesses. In this embodiment, the processing module 910 is operable to validate (namely, when in operation, the processing module 910 validates) target positions of genes that are susceptible to causing fetal illnesses.

In an embodiment, the prenatal screening system 800 differentiates in operation (namely, is operable to differentiate) maternal and fetal components of cell-free DNA, wherein, in this embodiment, such differentiation may be achieved by employing an assay design which enriches the fetal component and which aids in mapping of maternal and fetal reads.

In another exemplary embodiment, the prenatal screening system 800 designs or selects baits in operation (namely, is operable to design or select baits) and employs the baits at targeted positions on the genes that are susceptible to causing fetal illnesses for enrichment by hybridization; such a design is beneficially implemented in a recursive manner as the prenatal screening system 800 enlarges its databases of information as a result of processing many biological samples over a period of many years. Furthermore, the prenatal screening system 800 avoids, alternatively enriches, (namely, is operable to avoid, alternatively enrich) the maternal-specific regions in the blood sample.

Figure 10:
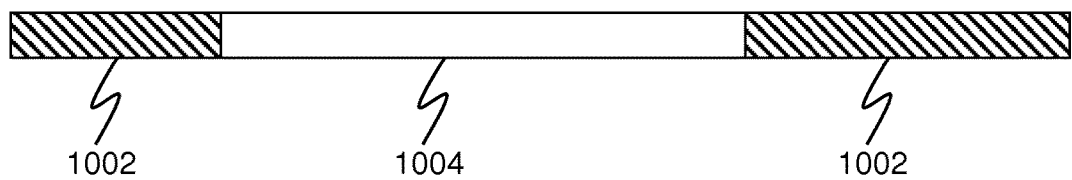
FIG. 10 is an illustration of molecular barcode-ligated DNA fragments, in accordance with an embodiment of the present disclosure.

Referring to FIG. 10, there is shown an illustration of molecular barcode (UMI)-ligated DNA fragments 1000, in accordance with an embodiment of the present disclosure. The prenatal screening system 800 ligates in operable (namely, is operable to ligate) nucleic acid base molecular barcodes 1002 to fragments of the cell-free DNA 1004 present in the blood sample. Optionally, the nucleic acid base molecular barcodes 1002 may be ligated to fragments of cell-free DNA 1004 and may be followed by subsequent enrichment by hybridization using baits targeted at genes that are susceptible to causing fetal illnesses.

In an embodiment, the prenatal screening system 800 implements in operation (namely, is operable to implement) the molecular barcode (UMI) 1002 as an n-mer. Optionally, n is in a range of 3 to 100. More optionally, n is in a range of 4 to 20. Yet more optionally, n is substantially 10.

Specifically, the molecular barcode 1002 may be implemented in a range of 3-mer to 100-mer.

In an embodiment, the molecular barcode 1002 includes a random sequence of nucleic acid bases. Specifically, the nucleic acid bases include adenine (A), cytosine (C), guanine (G), thymine (T).

In an embodiment, the molecular barcode 1002 includes adapters (namely, linkers). Specifically, adapters are short, chemically synthesized, single-stranded or double-stranded oligonucleotide. More specifically, such adapters may be comprised in the molecular barcode 1002 and may facilitate ligation thereof.

According to an embodiment, start sites for ligating the molecular barcode 1002 are determined by enzymic digestion. As aforementioned, fragments of cell-free DNA are enriched in the prenatal screening system 800. Furthermore, start sites may be generated on the fragments of cell-free DNA during enzymatic shearing of the cell-free DNA.

Figure 11:
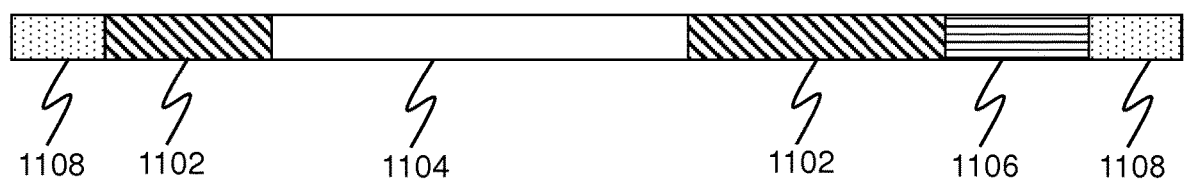
FIG. 11 is an illustration of amplified molecular barcode-ligated fragment, in accordance with an embodiment of the present disclosure.

Referring to FIG. 11, there is shown an illustration of amplified molecular barcode-ligated fragment 1100, in accordance with an embodiment of the present disclosure; however, it is will be appreciated that the unique molecular barcode may not be example in a position as illustrated. The prenatal screening system 800 amplifies in operation (namely, is operable to amplify) the molecular barcode-ligated DNA fragments 1000 for sequencing the amplified molecular barcode-ligated fragments 1100. Specifically, the molecular barcode-ligated DNA fragments 1000 are amplified by the prenatal screening arrangement 800. Optionally, the amplification may include using a Polymerase Chain Reaction (PCR) technique. Specifically, such amplification techniques may amplify a single copy or a few copies of a molecular barcode-ligated DNA fragments 1000 by several orders of magnitude, thereby generating potentially thousands of millions of copies of the particular given DNA sequence. Furthermore, such amplification techniques may provide an error, such as duplication of a nucleic acid base, in such an amplification process, which may be incorrectly represented as indicative of a genetic abnormality. Furthermore, such error may be corrected during sequencing of the amplified molecular barcode-ligated fragments 1100. Consequently, the cell-free DNA readout data generated from sequencing process of the amplified molecular barcode-ligated fragments 1100 may take into account the amplification error when generating, namely computing, the risk score.

In an embodiment, the amplified molecular barcode-ligated fragments 1100 comprise the molecular barcodes 1102 (such as the molecular barcodes 1002), fragments of the cell-free DNA 1104 (such as the fragments of the cell-free DNA 1004). Furthermore, the amplified molecular barcode-ligated fragments 1100 may comprise a sample-specific index 1108. Specifically, the sample-specific index 1108 comprises a pre-defined sequence and a random 8-mer molecular barcode. Furthermore, if an error, such as the duplication of a nucleic acid base, is generated during the amplification process, the sample-specific index may be used during sequencing to identify the amplification error. Additionally, sites may represent sites for amplification, wherein amplified DNA may be attached to the sites. Alternatively, or additionally, optionally, the sites may comprise baits used to perform hybridization enrichment of targeted genes that are susceptible to causing fetal illnesses.

The amplified molecular barcode-ligated fragments 1100 are sequenced to generate cell-free DNA readout data. Optionally, sequencing process may account for errors generated during an amplification process or processes. More optionally, the cell-free DNA readout data is indicative of whether or not there are genetic abnormalities in the blood sample. Optionally, (for example) the skeletal abnormality and/or the cardiac abnormality is caused by a de novo mutation. Furthermore, the molecular barcode-ligated fragments are useful to employ for reducing stochastic noise (namely, stochastic error) generated during aforementioned sequencing process and/or during processing in the data processing arrangement 804.

In an embodiment, the wet-laboratory arrangement 802 incorporates in operation (namely, is operable to incorporate) the molecular barcode to a cell-free DNA library containing a fetal component, and uses the cell-free DNA library thereby obtained in hybridisation-based enrichment for identifying de novo variants when computing the risk score. Specifically, the wet-laboratory arrangement prepares, in operation, (namely, is operable to prepare) a cell-free DNA library comprising information about cell-free DNA readout data and the molecular barcodes. Furthermore, the cell-free DNA library may be used in achieving a higher accuracy of identification of de novo variants in a given fetal DNA.

Figure 12:
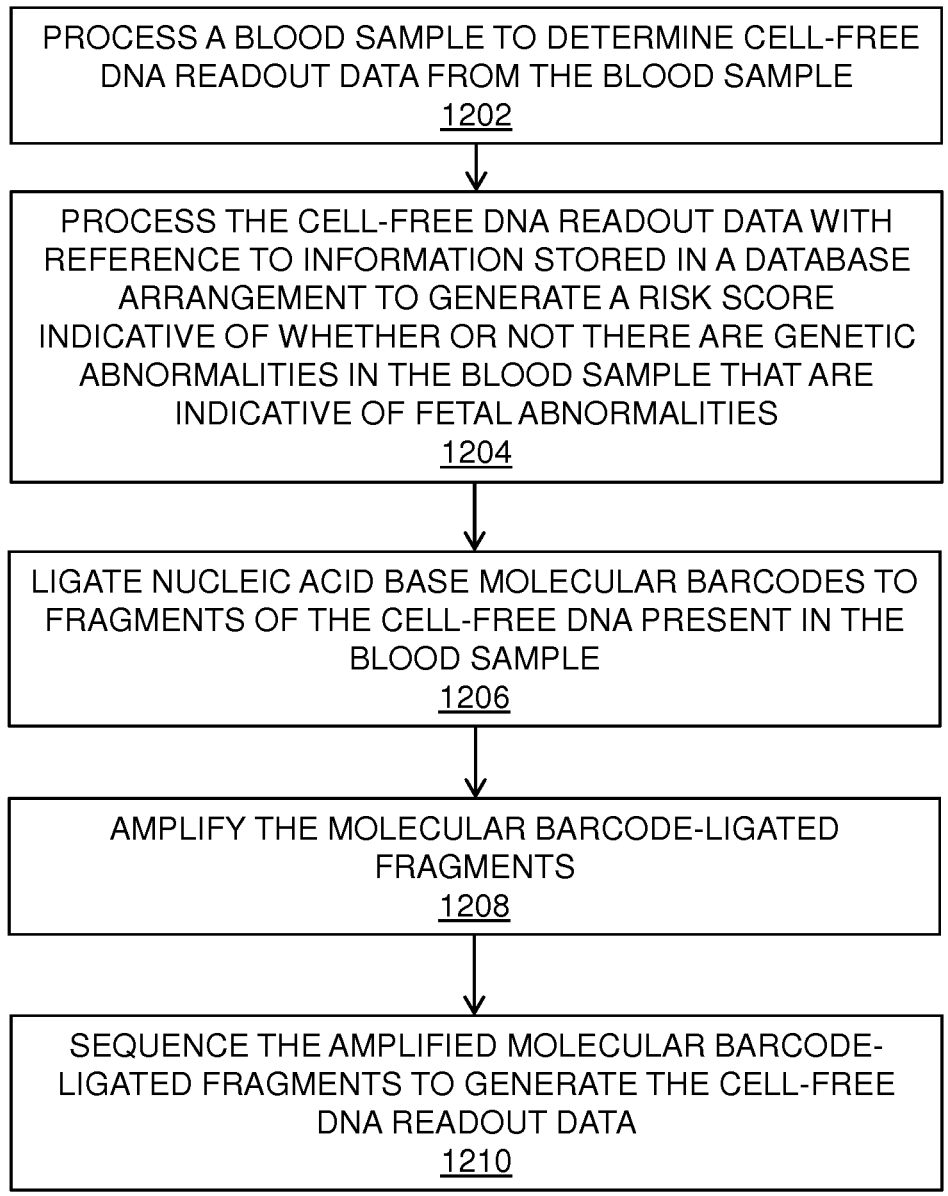
FIG. 12 is an illustration of steps of a method of (for) using the prenatal screening system of FIG. 8, in accordance with an embodiment of the present disclosure.

Referring to FIG. 12, there is shown an illustration of steps of a method 1200 of (for) using a prenatal screening system (such as the prenatal screening system 800 of FIG. 8), in accordance with an embodiment of the present disclosure. At a step 1202, a blood sample is processed to determine cell-free DNA readout data from the blood sample. At a step 1204, the cell-free DNA readout data is processed with reference to information stored in a database arrangement (for example the aforementioned knowledge base) to generate, namely to compute, a risk score indicative of whether or not there are genetic abnormalities in the blood sample that are indicative of fetal abnormalities. At a step 1206, nucleic acid base molecular barcodes are ligated to fragments of the cell-free DNA present in the blood sample. At a step 1208, the molecular barcode-ligated fragments are amplified. At a step 1210, the amplified molecular barcode-ligated fragments are sequenced to generate the cell-free DNA readout data.

The steps 1202 to 1210 are only illustrative and other alternatives can also be provided where one or more steps are added, one or more steps are removed, or one or more steps are provided in a different sequence without departing from the scope of the claims herein. Optionally, the method 1200 includes operating the prenatal screening system to implement the molecular barcode as an n-mer, wherein n is in a range 3 to 100. Optionally, the method 1200 includes arranging for the molecular barcode to include a random sequence of nucleic acid bases. More optionally, the method 1200 includes generating fragments of cell-free DNA in the prenatal screening system by employing enzymic digestion. Yet more optionally, the method 1200 includes determining start sites for ligating the molecular barcode by the enzymic digestion.

Optionally, the method 1200 includes operating the wet-laboratory arrangement to incorporate the molecular barcode to a cell-free DNA library containing a fetal component, and to use the cell-free DNA library thereby obtained in hybridisation-based enrichment for identifying de novo variants when computing the risk score. Optionally, the method 1200 includes operating the prenatal screening system to generate the cell-free DNA fragments by employing enzymic digestion, to ligate nucleic acid base molecular barcodes to the fragments to generate corresponding barcoded fragments, and to perform enrichment by hybridization using baits targeted at genes which for one or more diseases that are susceptible to causing fetal illnesses. More optionally, the method 1200 includes operating the prenatal screening system to perform non-invasive molecular diagnosis of a fetus which on ultrasound investigation (for example, non-invasive ultrasound imaging) presents with a skeletal abnormality and/or a cardiac abnormality. Yet more optionally, the skeletal abnormality and/or the cardiac abnormality is caused by a de novo mutation.

Optionally, the aforementioned method 1200 of (for) using the prenatal screening system is implemented by using a computer program product comprising a non-transitory computer-readable storage medium having computer-readable instructions stored thereon, the computer-readable instructions being executable by a computerized device comprising processing hardware.

Although use of the prenatal screening system 800 is described in the foregoing, it will be appreciated that the prenatal screening system may be used for investigating other types of biological problems, and not merely restricted to prenatal screening tasks, for example: cancer risk determination; autistic risk determination; verification of organism performance after performing gene therapy; ionizing radiation damage identification to cell DNA; and/or diabetes risk determination.

Figure 13:
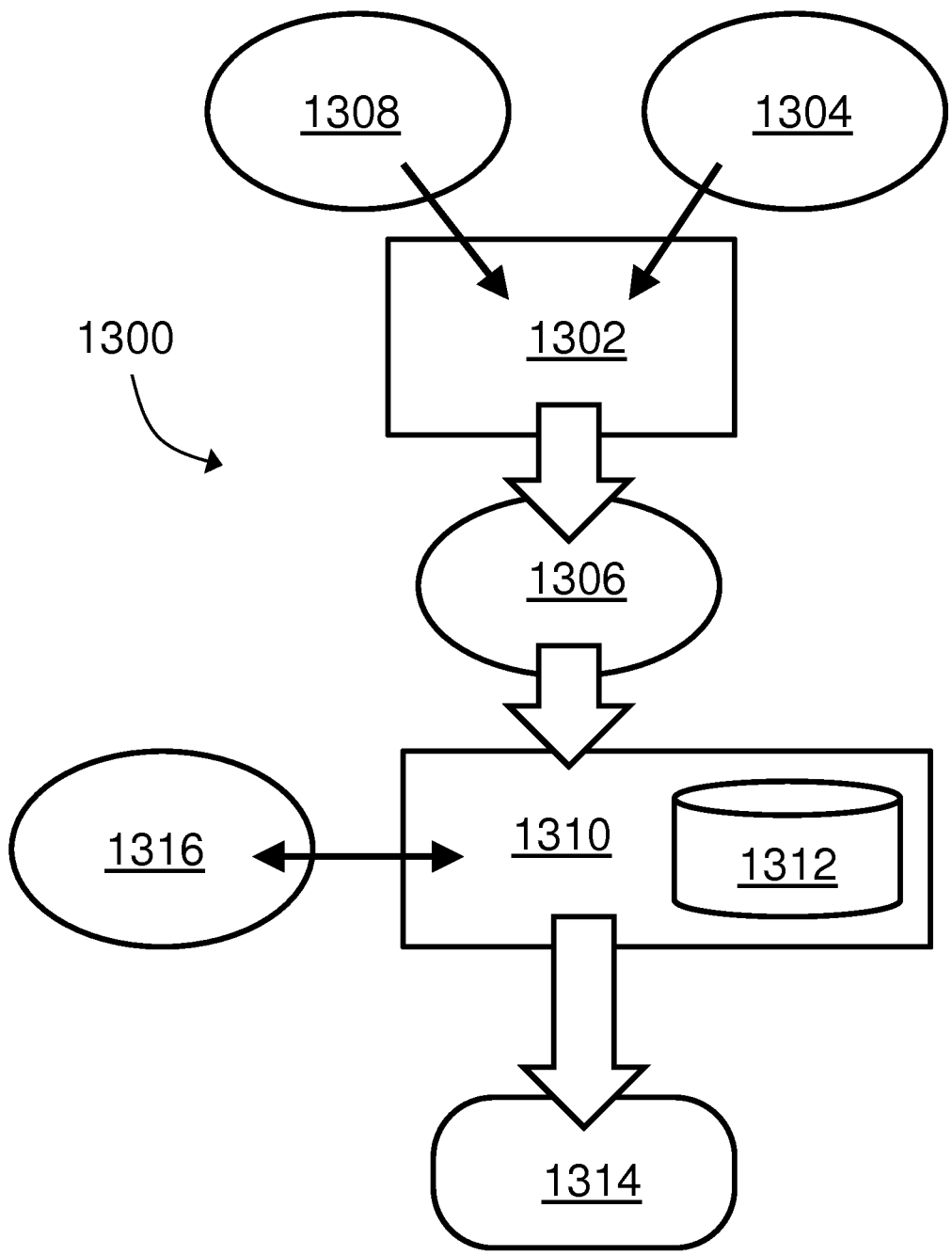
FIG. 13 is an illustration of a screening system employing a combination of a plurality of the screening systems illustrated in FIG. 1, FIG. 4, FIG. 6 and FIG. 8.

In overview, referring to FIG. 13, the present disclosure is concerned with a screening system 1300 that includes:

(i) a wet laboratory arrangement 1302 that processes, when in operation, biological samples 1304 to generate corresponding measurement data 1306, using one or more reagents 1308; and (ii) a data processing arrangement 1310 that executes a computer software product 1312 to process the measurement data 1306 to generate output data 1314 from the screening system 1300, wherein the output data 1314 includes information that is derived from the processed biological samples 1304, and provides a risk score in relation to a donor of the biological samples 1304. The biological samples 1304 include, for example, a maternal blood sample from a given mother when in a non-pregnant state and a maternal blood sample from the given mother when in a pregnant state. The measurement data 1306 is processed, for example, with reference to secondary data 1316 that is, for example, derived from inspection of the given mother, for example by using ultrasound scans, collecting data describing a family history of the given mother, lifestyle parameters of the given mother (for example smoker or non-smoker, obesity, alcoholic or non-alcoholic, narcotic substance abuser, a medical history of the given mother (for example, previous infectious disease experienced by the given mother), a medication history of the given mother (for example, treatment, surgery and medicines consumed by the given mother) and so forth. Optionally, the secondary data 1316 includes information describing characteristics of a child being borne via pregnancy by the given mother. Moreover, the measurement data 1306 also includes a genome database including information describing various genetic illnesses and gene morphisms or polymorphisms that give rise to the various genetic illnesses.

In an exemplary embodiment, the DNA fragment isolated from the biological sample is indicative of heart problems and the mother has pre-existing genetic defects indicative of heart problems. Therefore, there exists a risk that the foetus may be afflicted with such problems, unless foetal DNA fragments do not show such defects. In such a situation, using the secondary data (for example, "amniocentesis" samples and/or high-resolution ultrasound scanning of the foetus) may reduce the risk of error for determining the genetic defects indicative of heart problems in the foetus.

In the following description of embodiments of the disclosure, there is described a screening system 100 in respect of FIG. 1, a screening system 400 in respect of FIG. 4, a screening system 600 in respect of FIG. 6, and a screening system 800 in respect of FIG. 8; the screening system 1300 includes one or more of the screening systems 100, 400, 600, 800, for example the screening system 1300 includes a combination of a plurality of the screening systems 100, 400, 600, 800. The screening system 100 is distinguished, for example, by its use of baits; the baits are used for capturing cell-free DNA (cfDNA) fragments of maternal origin and fetal origin derived from a given maternal blood sample after centrifugal removal of red corpuscles to which the baits are applied; the baits include a length of N base pairs, wherein N is in a range of 50 to 2000 base pairs, more optionally in a range of 100 to 200 base pairs, and yet more optionally 120 base pairs. Optionally, a mixture of 1000 to 20000 different baits, for example 10000 different baits, are applied to the blood plasma after removal of red corpuscles. For example, the supplied baits are at least one of a shelf and custom baits from Agilent® and/or Nimblegene®. Furthermore, the supplied baits may be DNA or RNA of 120 base pairs (bp), for example. The screening system 400 is distinguished, for example, in its use of data processing to remove stochastic errors from DNA reads in relation to secondary information that provides information indicative of which parts of a given gene is likely to suffer a relatively higher degree of readout error. The screening system 600 is distinguished, for example, in its use of secondary data describing a donor of the blood sample for modifying data processing performed in the data processing arrangement for processing selective regions of the cell-free DNA readout data when generating the risk score; for example, the selective regions are determined by accessing one or more databases of a database arrangement, wherein the prenatal screening system 600 is updates in operation (namely, is operable to update) the one or more databases recursively or iteratively depending upon a determined accuracy of the risk score to one or more subsequent fetal investigations. The screening system 800 is distinguished, for example, in that it employs a data processing arrangement for processing the cell-free DNA readout data with reference to information stored in a database arrangement to generate, namely to compute, a risk score indicative of whether or not there are genetic abnormalities in a blood sample that are indicative of fetal abnormalities, wherein the prenatal screening system is operable to ligate nucleic acid base molecular barcodes to fragments of the cell-free DNA present in the blood sample prior to amplifying the molecular barcode-ligated DNA fragments for sequencing the amplified molecular barcode-ligated fragments to generate the cell-free DNA readout data. For example, various different barcodes can be used in combination with baits of various lengths, namely a combination of the screening system 100 and the screening system 800, so that a single PCR DNA readout operation can be used for sequencing all the cfDNA fragments in respect of all the baits of different lengths as a function of lengths of the baits, to try to reduce stochastic errors or ambiguities in measurement when using the system 1300.

In an embodiment, molecular barcodes employed are members of a minimally cross-hybridizing set. Specifically, the nucleotide sequence of each member of such a set is sufficiently different from that of every other member of the set that no member may form a stable duplex with the complement of any other member under stringent hybridization conditions. Alternatively, the nucleotide sequence of each member of a minimally cross-hybridizing set differs from those of every other member by at least two nucleotides.

In some embodiments, a nucleic acid barcode is often a nucleic acid of a particular sequence that is incorporated within, or appended to (for example, associated with) a specific nucleic acid, or subset of nucleic acids of a sample to track and/or identify the specific nucleic acid, or subset of nucleic acids, in a mixture of nucleic acids. In certain embodiments, a distinguishable nucleic acid barcode comprises a distinguishable sequence of nucleotides usable as an identifier to allow unambiguous identification of one or more nucleic acids (for example, a subset of nucleic acids) within a sample, method or assay. A distinguishable nucleic acid barcode is often, in embodiments of the present disclosure, configured to allow unambiguous identification of the origin or identity of a nucleic acid to which the barcode is associate with.

In some embodiments, a distinguishable nucleic acid barcode (for example, a barcode) can allow identification of the source of a particular nucleic acid in a mixture of nucleic acids obtained from difference sources.

In some embodiments, a distinguishable nucleic acid barcode is configured (for example, designed, synthesized or selected from a library) to allow (namely, to enable) unambiguous identification of the origin or identity of a nucleic acid to which the barcode is associated with. For example, in certain embodiments a distinguishable nucleic acid barcode is specific and/or unique to a certain sample, sample source, a library of nucleic acids obtained from the same subject or tissue, a particular nucleic acid genus or subset, a particular nucleic acid species, nucleic acids from the same chromosome, the like or combinations thereof.

In some embodiments, nucleic acids comprising inserts are employed that are derived from a sample, subject or tissue include a nucleic acid barcode that is specific and unique to the sample, subject or tissue thereby allowing unambiguous identification of the nucleic acid and/or insert from a nucleic acid derived from a different sample, subject or tissue. Accordingly, a distinguishable nucleic acid barcode that is unique to a sample, subject or tissue, is often distinguishable, in embodiments of the present disclosure, from, and different from, other nucleic acid barcodes in a mixture of nucleic acids.

In some embodiments of the present disclosure, a distinguishable nucleic acid barcode that is unique is different and/or is distinguishable from other barcodes in a composition comprising one or more samples derived from one or more sources (for example, a library of nucleic acid derived from different samples or sources). In some embodiments, a distinguishable nucleic acid barcode that is unique to a sample, subject or tissue is associated with (for example, contained within) nucleic acids derived from the same sample, subject, tissue, or a particular subset thereof. Accordingly, in some embodiments of the present disclosure, nucleic acids derived from the same sample, subject, or tissue often comprise at least one distinguishable nucleic acid barcode of identical sequence that is associated with each nucleic acid of the same sample, subject, or tissue.

In an exemplary embodiment, the barcodes may each have a length within a range of 4 to 36 nucleotides, more optionally in a range of 6 to 30 nucleotides, yet more optionally in a range of 8 to 20 nucleotides. In certain example embodiments, melting temperatures of barcodes within a set are within a temperature band having a temperature range of 10° C. of one another, more optionally 5° C. of one another, or yet more optionally within 2° C. of one another. Modifications to embodiments described in the foregoing are possible without departing from the scope of the invention as defined by the accompanying claims. Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

REFERENCES

[1] Chan, K. C. A., Jiang, P., Sun, K., Cheng, Y. K. Y., Tong, Y. K., Cheng, S. H., . . . Lo, Y. M. D. (2016). Second generation noninvasive fetal genome analysis reveals de novo mutations, single-base parental inheritance, and preferred DNA ends. *Proceedings of the National Academy of Sciences*, 113(50), E8159-E8168. https://doi.org/10.1073/pnas.1615800113

[2] Chandrananda, D., Thorne, N. P., Bahlo, M., Tam, L.-S., Liao, G., & Li, E. (2015). High-resolution characterization of sequence signatures due to non-random cleavage of cell-free DNA. *BMC Medical Genomics*, 8(1), 29. https://doi.org/10.1186/s12920-015-0107-z

[3] Dhallan, R., Au, W.-C., Mattagajasingh, S., Emche, S., Bayliss, P., Damewood, M., . . . Mohr, M. (2004). Methods to Increase the Percentage of Free Fetal DNA Recovered From the Maternal Circulation. *JAMA*, 291(9), 1114. https://doi.org/10.1001/jama.291.9.1114

[4] Li, Y., Di Naro, E., Vitucci, A., Zimmermann, B., Holzgreve, W., & Hahn, S. (2005). Detection of Paternally Inherited Fetal Point Mutations for β-Thalassemia Using Size-Fractionated Cell-Free DNA in Maternal Plasma. *JAMA*, 293(7), 843. https://doi.org/10.1001/jama.293.7.843

[5] Lun, F. M. F., Tsui, N. B. Y., Chan, K. C. A., Leung, T. Y., Lau, T. K., Charoenkwan, P., . . . Lo, Y. M. D. (2008). Noninvasive prenatal diagnosis of monogenic diseases by digital size selection and relative mutation dosage on DNA in maternal plasma. *Proceedings of the National Academy of Sciences of the United States of America*, 105(50), 19920-5. https://doi.org/10.1073/pnas.0810373105

[6] Snyder, M. W., Kircher, M., Hill, A. J., Daza, R. M., & Shendure, J. (2016). Cell-free DNA Comprises an In Vivo Nucleosome Footprint that Informs Its Tissues-Of-Origin. *Cell*, 164(1-2), 57-68. https://doi.org/10.1016/j.cell.2015.11.050

[7] Strayer, R., Oudejans, C. B. M., Sistermans, E. A., & Reinders, M. J. T. (2016). Calculating the fetal fraction for noninvasive prenatal testing based on genome-wide nucleosome profiles. *Prenatal Diagnosis*, 36(7), 614-621. https://doi.org/10.1002/pd.4816

[8] Vainshtein, Y., Rippe, K., & Teif, V. B. (2017). NucTools: analysis of chromatin feature occupancy profiles from high-throughput sequencing data. *BMC Genomics*, 18(1), 158. https://doi.org/10.1186/s12864-017-3580-2

[9] Yang, Q., Du, Z., Song, Y., Gao, S., Yu, S., Zhu, H., . . . Zhang, G. (2017). Size-selective separation and overall-amplification of cell-free fetal DNA fragments using PCR-based enrichment. *Scientific Reports*, 7, 40936. https://doi.org/10.1038/srep40936

[10] Chan, L. L., and Jiang, P. (2015). Bioinformatics analysis of circulating cell-free DNA sequencing data. Clin. Biochem. 48, pp 962-975.

[11] Chan, K. C. A., Jiang, P., Sun, K., Cheng, Y. K. Y., Tong, Y. K., Cheng, S. H., Wong, A. I. C., Hudecova, I., Leung, T. Y., Chiu, R. W. K., et al. (2016). Second generation noninvasive fetal genome analysis reveals de novo mutations, single-base parental inheritance, and preferred DNA ends. Proc. Natl. Acad. Sci. U.S.A. 201615800.

[12] Chiu, R. W. K., Chan, K. C. A., Gao, Y., Lau, V. Y. M., Zheng, W., Leung, T., Foo, C. H. F., Xie, B., Tsui, N. B. Y., Lun, F. M. F., et al. (2008). Noninvasive prenatal diagnosis of fetal chromosomal aneuploidy by massively parallel genomic sequencing of DNA in maternal plasma. Proc. Natl. Acad. Sci. U.S.A. 105, pp 20458-20463.

[13] Kitzman, J. O., Snyder, M. W., Ventura, M., Lewis, A. P., Simmons, L. E., Gammill, H. S., Rubens, C. E., Santillan, D. a., Murray, J. C., Tabor, H. K., et al. (2012). Non-invasive Whole Genome Sequencing of Human Fetus. Sci. Transl. Med. 4, pp 1-18.

[14] Lam, K. W. G., Jiang, P., Liao, G. J. W., Chan, K. C. A., Leung, T. Y., Chiu, R. W. K., and Lo, Y. M. D. (2012). Noninvasive prenatal diagnosis of monogenic diseases by targeted massively parallel sequencing of maternal plasma: Application to ??-thalassemia. Clin. Chem. 58, pp 1467-1475.

[15] Lo, Y. M. D., Chan, K. C. A., Sun, H., Chen, E. Z., Jiang, P., Lun, F. M. F., Zheng, Y. W., Leung, T. Y., Lau, T. K., Cantor, C. R., et al. (2010). Maternal Plasma DNA Sequencing Reveals the Genome-Wide Genetic and Mutational Profile of the Fetus. Sci. Transl. Med. 2, 61ra91-61ra91.

[16] New, M. I., Tong, Y. K., Yuen, T., Jiang, P., Pina, C., Chan, K. C. A., Khattab, A., Liao, G. J. W., Yau, M., Kim, S.-M., et al. (2014). Noninvasive prenatal diagnosis of congenital adrenal hyperplasia using cell-free fetal DNA in maternal plasma. J. Clin. Endocrinol. Metab. 99, E1022-30.

[17] Xiong, L., Barrett, A. N., Hua, R., Tan, T. Z., Ho, S. S. Y., Chan, J. K. Y., Zhong, M., and Choolani, M. (2015). Non-invasive prenatal diagnostic testing for β-thalassaemia using cell-free fetal DNA and next generation sequencing. Prenat. Diagn. 35, pp 258-265.

[18] Chan, K. C. A., Jiang, P., Sun, K., Cheng, Y. K. Y., Tong, Y. K., Cheng, S. H., Wong, A. I. C., Hudecova, I., Leung, T. Y., Chiu, R. W. K., et al. (2016). Second generation noninvasive fetal genome analysis reveals de novo mutations, single-base parental inheritance, and preferred DNA ends. Proc. Natl. Acad. Sci. U.S.A. 201615800.

[19] Chandrananda, D., Thorne, N. P., and Bahlo, M. (2015). High-resolution characterization of sequence signatures due to non-random cleavage of cell-free DNA. BMC Med. Genomics 8, 29.

[20] New, M. I., Tong, Y. K., Yuen, T., Jiang, P., Pina, C., Chan, K. C. A., Khattab, A., Liao, G. J. W., Yau, M., Kim, S.-M., et al. (2014). Noninvasive prenatal diagnosis of congenital adrenal hyperplasia using cell-free fetal DNA in maternal plasma. J. Clin. Endocrinol. Metab. 99, E1022-30.

[21] Yu, S. C. Y., Chan, K. C. A., Zheng, Y. W. L., Jiang, P., Liao, G. J. W., Sun, H., Akolekar, R., Leung, T. Y., Go, A. T. J. I., van Vugt, J. M. G., et al. (2014). Size-based molecular diagnostics using plasma DNA for noninvasive prenatal testing. Proc. Natl. Acad. Sci. U.S.A. 111, pp 8583-8588.

[22] Chan, L. L., and Jiang, P. (2015). Bioinformatics analysis of circulating cell-free DNA sequencing data. Clin. Biochem. 48, pp 962-975.

[23] Chan, K. C. A., Jiang, P., Sun, K., Cheng, Y. K. Y., Tong, Y. K., Cheng, S. H., Wong, A. I. C., Hudecova, I., Leung, T. Y., Chiu, R. W. K., et al. (2016). Second generation noninvasive fetal genome analysis reveals de novo mutations, single-base parental inheritance, and preferred DNA ends. Proc. Natl. Acad. Sci. U.S.A. 201615800.

[24] Chiu, R. W. K., Chan, K. C. A., Gao, Y., Lau, V. Y. M., Zheng, W., Leung, T., Foo, C. H. F., Xie, B., Tsui, N. B. Y., Lun, F. M. F., et al. (2008). Noninvasive prenatal diagnosis of fetal chromosomal aneuploidy by massively parallel genomic sequencing of DNA in maternal plasma. Proc. Natl. Acad. Sci. U.S.A. 105, pp 20458-20463.

[25] Kitzman, J. O., Snyder, M. W., Ventura, M., Lewis, A. P., Simmons, L. E., Gammill, H. S., Rubens, C. E., Santillan, D. a., Murray, J. C., Tabor, H. K., et al. (2012). Non-invasive Whole Genome Sequencing of Human Fetus. Sci. Transl. Med. 4, pp 1-18.

[26] Lam, K. W. G., Jiang, P., Liao, G. J. W., Chan, K. C. A., Leung, T. Y., Chiu, R. W. K., and Lo, Y. M. D. (2012). Noninvasive prenatal diagnosis of monogenic diseases by targeted massively parallel sequencing of maternal plasma: Application to ??-thalassemia. Clin. Chem. 58, pp 1467-1475.

[27] Lo, Y. M. D., Chan, K. C. A., Sun, H., Chen, E. Z., Jiang, P., Lun, F. M. F., Zheng, Y. W., Leung, T. Y., Lau, T. K., Cantor, C. R., et al. (2010). Maternal Plasma DNA Sequencing Reveals the Genome-Wide Genetic and Mutational Profile of the Fetus. Sci. Transl. Med. 2, 61ra91-61ra91.

[28 New, M. I., Tong, Y. K., Yuen, T., Jiang, P., Pina, C., Chan, K. C. A., Khattab, A., Liao, G. J. W., Yau, M., Kim, S.-M., et al. (2014). Noninvasive prenatal diagnosis of congenital adrenal hyperplasia using cell-free fetal DNA in maternal plasma. J. Clin. Endocrinol. Metab. 99, E1022-30.

[29] Xiong, L., Barrett, A. N., Hua, R., Tan, T. Z., Ho, S. S. Y., Chan, J. K. Y., Zhong, M., and Choolani, M. (2015). Non-invasive prenatal diagnostic testing for β-thalassaemia using cell-free fetal DNA and next generation sequencing. Prenat. Diagn. 35, pp 258-265.

The invention claimed is:

1. A screening system comprising:
a wet-laboratory arrangement configured to determine a presence of cell-free DNA fragments in a biological sample comprising one or more maternal blood samples from a pregnant mother by enriching cell free fetal DNA fragments present in cell-free DNA derived from plasma of the one or more maternal blood samples that start within a nucleosome and have a shorter nucleic acid base count than an average length nucleic acid base count of cell-free DNA in the one or more maternal blood samples to sequence the cell-free DNA fragments; and
a data processing arrangement comprising a non-transitory computer-readable storage medium comprising computer instructions, wherein the data processing arrangement under control of the computer instructions is configured to:
compare information representative of the sequenced DNA fragments against information stored in a genomic database arrangement to provide an assessment score with respect to the biological sample; and
apply a modification to one or more stochastic ratings associated with the information representative of the sequenced DNA fragments using secondary information provided to the screening system to reduce a stochastic and/or systemic uncertainty present in the assessment score.

2. The screening system according to claim 1, wherein the wet-laboratory arrangement is further configured to distinguish between cell-free DNA fragments of maternal origin and cell-free DNA fragments of placental and/or fetal origin.

3. The screening system according to claim 1, wherein the data processing arrangement is further configured to employ at least one of the following scores when computing the modification in the data processing arrangement:
a genome locality score, wherein the genome locality score includes a likelihood of a mutation within a region;
a sequence error score, wherein the sequence error score includes a likelihood of a given nucleic acid base being a result of PCR infidelity during template amplification and/or a miscall during a sequencing process;
a patient modifier score, wherein the patient modifier score includes information from external sources; and
a mosaicism detection score, wherein the mosaicism detection score includes a likelihood of variants occurring in a region of imbalanced maternal genotype.

4. The screening system according to claim 3, wherein the data processing arrangement is further configured to calculate the likelihood of mutation within the region on a basis of frequencies of change susceptible to occur to the region and/or frequencies of calling spurious variants in the region.

5. The screening system according to claim 3, wherein the data processing arrangement is further configured to calculate the sequence error score using a maternal genetic sequence.

6. The screening system according to claim 3, wherein the information from external sources includes at least information received from abnormality scans.

7. The screening system according to claim 3, wherein the data processing arrangement is further configured to convert the genome locality score into a weight for a particular locus.

8. The screening system according to claim 3, wherein the data processing arrangement is further configured to apply the sequence error score as a weight and to modify confidence in a base call.

9. The screening system according to claim 3, wherein the data processing arrangement is further configured to convert the details from external sources into a weight.

10. The screening system according to claim 3, wherein the data processing arrangement is further configured to combine the genome locality score, the sequence error score, the patient modifier score and/or mosaicism detection score to modify the confidence of a call.

11. The screening system according to claim 3, wherein the biological sample containing cell-free DNA fragments therein is extracted from a pregnant woman in a non-invasive manner.

12. The screening system of claim 1 wherein the enrichment utilizes baits based upon coordinates of cell-free fetal DNA fragment specific end-points; and the data processing arrangement is configured to analyze the isolated free fetal DNA and compare it with one or more DNA templates stored in the data processing arrangement for determining an occurrence of one or more biological characteristics of fetal DNA present in the one or more maternal blood samples.

13. The screening system according to claim 12, wherein the wet-laboratory arrangement is configured to select baits designed to enrich fetal DNA present in the plasma.

14. The screening system according to claim 12, wherein the wet-laboratory arrangement is configured to perform a combined test for prenatal screening of fetal genetic abnormalities, wherein the combined test includes at least one of:

at least one maternal blood test; and an ultrasound scan of a fetus.

15. The screening system of claim 1, wherein the wet-laboratory arrangement is further configured for processing the biological sample as a blood sample to determine cell-free DNA readout data from the blood sample and the data processing arrangement is further configured for processing the cell-free DNA readout data with reference to information stored in a database arrangement to generate a risk score indicative of whether or not there are genetic abnormalities in the blood sample that are indicative of fetal abnormalities, wherein the wet-laboratory arrangement is still further configured to ligate nucleic acid base molecular barcodes to fragments of the cell-free DNA present in the blood sample prior to amplifying the molecular barcode-ligated DNA fragments for sequencing the amplified molecular barcode-ligated fragments to generate the cell-free DNA readout data.

16. The screening system of claim 15, wherein the wet-laboratory arrangement is still further configured to implement the molecular barcodes as an n-mer, wherein n is in a range of 3 to 100.

17. A method of using a screening system that:

processes in operation a biological sample comprising one or more maternal blood samples from a pregnant mother in a wet-laboratory arrangement configured to determine a presence of cell-free DNA fragments therein by enriching cell free fetal DNA fragments present in cell-free DNA derived from plasma of the one or more maternal blood samples that start within a nucleosome and have a shorter nucleic acid base count than an average length nucleic acid base count of cell-free DNA in the one or more maternal blood samples to sequence the DNA fragments; and uses in operation a data processing arrangement configured to compare information representative of the sequenced DNA fragments against information stored in a genomic database arrangement to provide an assessment score in respect of the biological sample, wherein the method includes operating the screening system to apply a modification to one or more stochastic ratings associated with the information representative of the sequenced DNA fragments using secondary information provided to the screening system to reduce a stochastic and/or systemic uncertainty present in the assessment score.

18. The method of using a screening system of claim 17, wherein the screening system includes a wet-laboratory arrangement for processing the biological sample as a blood sample to determine cell-free DNA readout data from the blood sample and a data processing arrangement for processing the cell-free DNA readout data with reference to information stored in a database arrangement to generate a risk score indicative of whether or not there are genetic abnormalities in the blood sample that are indicative of fetal abnormalities, wherein the method includes:

using the wet-laboratory arrangement for:

ligating nucleic acid base molecular barcodes to fragments of the cell-free DNA present in the blood sample;

amplifying the molecular barcode-ligated fragments; and sequencing the amplified molecular barcode-ligated fragments to generate the cell-free DNA readout data.

\* \* \* \* \*